United States Patent
Porro et al.

(10) Patent No.: US 6,630,330 B1
(45) Date of Patent: Oct. 7, 2003

(54) ASCORBIC ACID PRODUCTION FROM YEAST

(75) Inventors: Danilo Porro, Erba (IT); Michael Sauer, Mäder (AT)

(73) Assignee: Biopolo S.C.a.R.L., Milan (IT)

( * ) Notice: Subject to any disclaimer, the term of this patent is extended or adjusted under 35 U.S.C. 154(b) by 0 days.

(21) Appl. No.: 09/630,983

(22) Filed: Aug. 2, 2000

(51) Int. Cl.$^7$ ............... C12P 17/00; C12P 7/62
(52) U.S. Cl. ......... 435/117; 435/126; 435/135; 435/137; 435/254.21; 549/315
(58) Field of Search ............... 435/126, 135, 435/137, 254.21, 117; 549/315

(56) References Cited

U.S. PATENT DOCUMENTS

| | | |
|---|---|---|
| 4,595,659 A | 6/1986 | Roland et al. |
| 4,916,068 A | 4/1990 | Roland et al. |
| 2002/0012979 A1 * | 1/2002 | Berry et al. ............ 435/136 |

FOREIGN PATENT DOCUMENTS

| | | |
|---|---|---|
| WO | WO85/01745 | 4/1985 |
| WO | WO98/50558 | 11/1998 |
| WO | WO99/33995 | 7/1999 |
| WO | WO99/64618 | 12/1999 |
| WO | WO00/34502 | 6/2000 |

OTHER PUBLICATIONS

Berendsen A Glimpse of the Holy Grail Oct. 23, 1998 Vol 282 Science pp. 642–643.*
EMBL/GenBank/DDBJ Entry O81884.*
Darnis et al. Cloning, sequencing and functional expression of a cDNA encoding porcine pancreatic precarboxypeptidase A1. Feb. 1999. European Journal of Biochemistry 259: 719–725.*
Wheeler et al. The biosynthetic pathway of vitamin C in higher plants. May 1998. Nature 393:365–369.*
U.S. patent application Publication No. 2002/0076771 (published Jun. 20, 2002).
PCT/GB01/03485 International Search Report (Jul. 12, 2002).
Onofri et al., "Influence of L–Galactonic Acid γ–Lactone on Ascorbate Production in Some Yeasts," *Antonie van Leeuwenhoek* 71:227–280 (1997).
Krasnov et al., "Expression of Rat Gene for $_L$–Gulono–γ–Lactone Oxidase, the Key Enzyme of $_L$–Ascorbic Acid Biosynthesis, in Guinea Pig Cells and in Teleost Fish Rainbow Trout (*Oncorhynchus mykiss*)" *Biochimica et Biophysica Acta* 1381:241–248 (1998).
Kanagasundaram et al., "Isolation and Charaterization of the Gene Encoding Gluconolactonase from *Zymomonas mobilis*," *Biochimica et Biophysica Acta* 1171:198–200 (1992).
Koshizaka et al., *J. Biol. Chem.* 263:1619–1621 (1998).
Huh et al., *Mol. Microb.* 30:895–903 (1998).
Huh et al., *Eur. J. Biochem.* 225:1073–1079 (1994).
Kim et al., *Biochim. Biophys. Acta* 1297:1–8 (1996).
Kim et al., *Biochim. Biophys. Acta* 1429:29–39 (1998).
Dumbrava et al., *Biochim. Biophys. Acta* 926:331–338 (1987).
Nick et al., *Plant Science* 46:181–187 (1986).
Lee et al., *App. Env. Microb.* 65:4685–4687 (1999).
Østergaard et al., *J. Biol. Chem.* 272:30009–30016 (1997).
Hancock et al., *FEMS Microbiol. Lett.* 186:245–250 (2000).
Spickett et al., *Free Rad. Biol. Med.* 28:183–192 (2000).
Daruwala et al., *FEBS Lett.* 460:480–484 (1999).

* cited by examiner

*Primary Examiner*—David Suzu
*Assistant Examiner*—David A. Lambertson
(74) *Attorney, Agent, or Firm*—Williams, Morgan & Amerson, P.C.

(57) ABSTRACT

Herein is disclosed a method of generating ascorbic acid from yeast. In one embodiment, the yeast is a Zygosaccharomyces spp. or a Kluyveromyces spp. growing in a medium comprising an ascorbic acid precursor. In a second embodiment the yeast is a recombinant yeast growing in a medium comprising an ascorbic acid precursor. Preferably the recombinant yeast is transformed with a coding region encoding an enzyme selected from L-galactose dehydrogenase (LGDH), L-galactono-1,4-lactone dehydrogenase (AGD), D-arabinose dehydrogenase (ARA), D-arabinono-1,4-lactone oxidase (ALO) or L-gulono-1,4-lactone oxidase (RGLO). The ascorbic acid precursor is preferably D-glucose, L-galactose, L-galactono-1,4-lactone, or L-gulono-1,4-lactone. In another preferred embodiment the ascorbic acid is accumulated in the medium at levels greater than background. Preferably, the yield of the conversion of the precursor to ascorbic acid is preferably at least about 35%.

15 Claims, 7 Drawing Sheets

SEQUENCE LISTING

<160> NUMBER OF SEQ ID NOS: 26

<210> SEQ ID NO 1
<211> LENGTH: 610
<212> TYPE: PRT
<213> ORGANISM: Arabidopsis thaliana

<400> SEQUENCE: 1

```
Met Leu Arg Ser Leu Leu Leu Arg Arg Ser Val Gly His Ser Leu Gly
 1               5                  10                  15

Thr Leu Ser Pro Ser Ser Ser Thr Ile Arg Ser Ser Phe Ser Pro His
            20                  25                  30

Arg Thr Leu Cys Thr Thr Gly Gln Thr Leu Thr Pro Pro Pro Pro Pro
        35                  40                  45

Pro Pro Arg Pro Pro Pro Pro Pro Ala Thr Ala Ser Glu Ala Gln
    50                  55                  60

Phe Arg Lys Tyr Ala Gly Tyr Ala Ala Leu Ala Ile Phe Ser Gly Val
65                  70                  75                  80

Ala Thr Tyr Phe Ser Phe Pro Phe Pro Glu Asn Ala Lys His Lys Lys
                85                  90                  95

Ala Gln Ile Phe Arg Tyr Ala Pro Leu Pro Glu Asp Leu His Thr Val
            100                 105                 110

Ser Asn Trp Ser Gly Thr His Glu Val Gln Thr Arg Asn Phe Asn Gln
        115                 120                 125

Pro Glu Asn Leu Ala Asp Leu Glu Ala Leu Val Lys Glu Ser His Glu
    130                 135                 140

Lys Lys Leu Arg Ile Arg Pro Val Gly Ser Gly Leu Ser Pro Asn Gly
145                 150                 155                 160

Ile Gly Leu Ser Arg Ser Gly Met Val Asn Leu Ala Leu Met Asp Lys
                165                 170                 175

Val Leu Glu Val Asp Lys Glu Lys Lys Arg Val Thr Val Gln Ala Gly
            180                 185                 190

Ile Arg Val Gln Gln Leu Val Asp Ala Ile Lys Asp Tyr Gly Leu Thr
        195                 200                 205

Leu Gln Asn Phe Ala Ser Ile Arg Glu Gln Gln Ile Gly Gly Ile Ile
    210                 215                 220

Gln Val Gly Ala His Gly Thr Gly Ala Arg Leu Pro Pro Ile Asp Glu
225                 230                 235                 240

Gln Val Ile Ser Met Lys Leu Val Thr Pro Ala Lys Gly Thr Ile Glu
                245                 250                 255

Leu Ser Arg Glu Lys Asp Pro Glu Leu Phe His Leu Ala Arg Cys Gly
            260                 265                 270
```

Leu Gly Gly Leu Gly Val Val Ala Glu Val Thr Leu Gln Cys Val Ala
        275                 280                 285

Arg His Glu Leu Val Glu His Thr Tyr Val Ser Asn Leu Gln Glu Ile
        290                 295                 300

Lys Lys Asn His Lys Lys Leu Leu Ser Ala Asn Lys His Val Lys Tyr
305                 310                 315                 320

Leu Tyr Ile Pro Tyr Thr Asp Thr Val Val Val Thr Cys Asn Pro
                325                 330                 335

Val Ser Lys Trp Ser Gly Pro Pro Lys Asp Lys Pro Lys Tyr Thr Thr
                340                 345                 350

Asp Glu Ala Val Gln His Val Arg Asp Leu Tyr Arg Glu Ser Ile Val
        355                 360                 365

Lys Tyr Arg Val Gln Asp Ser Gly Lys Lys Ser Pro Asp Ser Ser Glu
        370                 375                 380

Pro Asp Ile Gln Glu Leu Ser Phe Thr Glu Leu Arg Asp Lys Leu Leu
385                 390                 395                 400

Ala Leu Asp Pro Leu Asn Asp Val His Val Ala Lys Val Asn Gln Ala
                405                 410                 415

Glu Ala Glu Phe Trp Lys Lys Ser Glu Gly Tyr Arg Val Gly Trp Ser
                420                 425                 430

Asp Glu Ile Leu Gly Phe Asp Cys Gly Gly Gln Gln Trp Val Ser Glu
        435                 440                 445

Ser Cys Phe Pro Ala Gly Thr Leu Ala Asn Pro Ser Met Lys Asp Leu
        450                 455                 460

Glu Tyr Ile Glu Glu Leu Lys Lys Leu Ile Glu Lys Glu Ala Ile Pro
465                 470                 475                 480

Ala Pro Ala Pro Ile Glu Gln Arg Trp Thr Ala Arg Ser Lys Ser Pro
                485                 490                 495

Ile Ser Pro Ala Phe Ser Thr Ser Glu Asp Asp Ile Phe Ser Trp Val
                500                 505                 510

Gly Ile Ile Met Tyr Leu Pro Thr Ala Asp Pro Arg Gln Arg Lys Asp
        515                 520                 525

Ile Thr Asp Glu Phe Phe His Tyr Arg His Leu Thr Gln Lys Gln Leu
        530                 535                 540

Trp Asp Gln Phe Ser Ala Tyr Glu His Trp Ala Lys Ile Glu Ile Pro
545                 550                 555                 560

Lys Asp Lys Glu Glu Leu Glu Ala Leu Gln Ala Arg Ile Arg Lys Arg
                565                 570                 575

Phe Pro Val Asp Ala Tyr Asn Lys Ala Arg Arg Glu Leu Asp Pro Asn
                580                 585                 590

Arg Ile Leu Ser Asn Asn Met Val Glu Lys Leu Phe Pro Val Ser Thr
        595                 600                 605

Thr Ala
    610

<210> SEQ ID NO 2
<211> LENGTH: 1833
<212> TYPE: DNA
<213> ORGANISM: Artificial Sequence
<220> FEATURE:
<223> OTHER INFORMATION: Description of Artificial Sequence: A. thaliana

<400> SEQUENCE: 2
atgctccggt cacttcttct ccgacgctcc gtcggccatt ctctcggaac cctatctccg      60
tcttcatcca ccatccgttc ctcatttttcg cctcatcgta ctctctgcac caccggtcaa    120

-continued

```
acattgacac caccaccgcc gccaccgcca cgtcctccac ctccgcctcc ggccaccgcc    180
tcagaagctc aattccgtaa atacgccgga tacgcagcac tcgctatctt ctctggagtt    240
gctacctatt tctcatttcc attccctgag aatgctaaac acaagaaggc tcaaatcttc    300
cgttacgctc ctttacctga agatcttcac actgtctcta attggagtgg tactcatgag    360
gtacagacta ggaactttaa tcaaccgag aatcttgctg atctcgaagc tcttgttaag     420
gaatctcatg agaagaagtt aaggattcgt cccgttggat cgggtctctc gcctaatggg    480
attggtttgt ctcgctctgg gatggtgaat ctggcgctta tggataaagt tctagaggtg    540
gataaagaga agaagagagt tacggtgcag gctgggatta gggtccagca attggttgac    600
gccattaaag actatggtct tactcttcag aactttgcct ccattagaga gcagcagatt    660
ggtggtatta ttcaggttgg ggcacatggg acaggtgcta gattgcctcc tattgatgag    720
caggtgatca gtatgaagct ggttactcct gcgaagggaa caattgaact ttcaagagag    780
aaagatccgg agctctttca tctagctcga tgtggccttg gtggacttgg agttgttgct    840
gaggtcaccc tccaatgcgt tgcaagacat gaacttgtgg aacacacata cgtctcaaac    900
ttgcaagaaa tcaagaaaaa tcacaaaaaa ttgctctctg caaacaagca tgttaagtac    960
ctatatattc cttataccga cacagtcgtg gttgtaacat gcaatcctgt atcaaaatgg   1020
agtgggccac ctaaggacaa accaaagtac actacagatg aggctgtaca gcatgtccgt   1080
gatctctaca gagagagcat tgtgaagtat agggtccagg actctggtaa gaagtctcct   1140
gacagcagtg agccagacat acaggagctt tcatttacag agttgagaga caaactactt   1200
gcccttgatc ctctcaatga cgttcacgtt gcaaaagtaa atcaagctga ggcagagttt   1260
tggaaaaaat cagaaggata tagagtaggg tggagtgatg aaattctggg ctttgactgt   1320
ggtggtcagc agtgggtgtc agaatcttgt tttcctgctg gaaccctcgc caaccctagc   1380
atgaaagacc ttgaatacat agaagagctg aaaaaactaa tagaaaagga agcaatacca   1440
gcacctgctc aatagagca gcgatggaca gctcgaagta agagccccat tagtcctgca   1500
ttcagcactt cagaggatga tattttctca tgggttggta taatcatgta cctcccgaca   1560
gcagaccctc gccagagaaa ggacatcaca gatgaatttt tccactatag acatttgaca   1620
cagaaacaat tgtgggatca attttctgcg tatgaacatt gggctaaaat tgagatacca   1680
aaagacaaag aagaacttga agccttacag gcaagaataa gaaaacgttt cccagtggat   1740
gcatacaaca aagcacgtag ggagctggac ccaaatagaa tcctctccaa caacatggtg   1800
gaaaagctct tcccagtctc caccactgct taa                                1833
```

<210> SEQ ID NO 3
<211> LENGTH: 600
<212> TYPE: PRT
<213> ORGANISM: Brassica oleracea

<400> SEQUENCE: 3

```
Met Leu Arg Ser Leu Leu Arg Arg Ser Asn Ala Arg Ser Leu Arg
  1               5                  10                  15

Pro Pro Phe Pro Pro Leu Arg Thr Leu Cys Thr Ser Gly Gln Thr Leu
                 20                  25                  30

Thr Pro Ala Pro Pro Pro Pro Pro Pro Pro Pro Ile Ser Ser
             35                  40                  45

Ser Ala Ser Glu Lys Glu Phe Arg Lys Tyr Ala Gly Tyr Ala Ala Leu
         50                  55                  60
```

```
Ala Leu Phe Ser Gly Ala Ala Thr Tyr Phe Ser Phe Pro Phe Pro Glu
 65                  70                  75                  80

Asn Ala Lys His Lys Ala Gln Ile Phe Arg Tyr Ala Pro Leu Pro
                 85                  90                  95

Glu Asp Leu His Thr Val Ser Asn Trp Ser Gly Thr His Glu Val Gln
                100                 105                 110

Thr Arg Asn Phe Asn Gln Pro Glu Thr Leu Ala Asp Leu Glu Ala Leu
            115                 120                 125

Val Lys Glu Ala His Glu Lys Lys Asn Arg Ile Arg Pro Val Gly Ser
        130                 135                 140

Gly Leu Ser Pro Asn Gly Ile Gly Leu Ser Arg Ser Gly Met Val Asn
145                 150                 155                 160

Leu Ala Leu Met Asp Lys Val Leu Glu Val Asp Lys Glu Lys Lys Arg
                165                 170                 175

Val Arg Val Gln Ala Gly Ile Arg Val Gln Gln Leu Val Asp Ala Ile
                180                 185                 190

Gln Glu Tyr Gly Leu Thr Leu Gln Asn Phe Ala Ser Ile Arg Glu Gln
            195                 200                 205

Gln Ile Gly Gly Ile Ile Gln Val Gly Ala His Gly Thr Gly Ala Arg
        210                 215                 220

Leu Pro Pro Ile Asp Glu Gln Val Ile Gly Met Lys Leu Val Thr Pro
225                 230                 235                 240

Ala Lys Gly Thr Ile Glu Leu Ser Lys Asp Asn Asp Pro Glu Leu Phe
                245                 250                 255

His Leu Ala Arg Cys Gly Leu Gly Gly Leu Gly Val Val Ala Glu Val
                260                 265                 270

Thr Leu Gln Cys Val Glu Arg Gln Glu Leu Leu Glu His Thr Tyr Val
        275                 280                 285

Ser Thr Leu Glu Glu Ile Lys Lys Asn His Lys Lys Leu Leu Ser Thr
        290                 295                 300

Asn Lys His Val Lys Tyr Leu Tyr Ile Pro Tyr Thr Asp Thr Val Val
305                 310                 315                 320

Val Val Thr Cys Asn Pro Val Ser Lys Trp Ser Gly Ala Pro Lys Asp
                325                 330                 335

Lys Pro Lys Tyr Thr Thr Glu Glu Ala Leu Lys His Val Arg Asp Leu
            340                 345                 350

Tyr Arg Glu Ser Ile Val Lys Tyr Arg Val Gln Asp Ser Ser Lys Lys
        355                 360                 365

Thr Pro Asp Ser Arg Glu Pro Asp Ile Asn Glu Leu Ser Phe Thr Glu
        370                 375                 380

Leu Arg Asp Lys Leu Ile Ala Leu Asp Pro Leu Asn Asp Val His Val
385                 390                 395                 400

Gly Lys Val Asn Gln Ala Glu Ala Glu Phe Trp Lys Lys Ser Glu Gly
                405                 410                 415

Tyr Arg Val Gly Trp Ser Asp Glu Ile Leu Gly Phe Asp Cys Gly Gly
            420                 425                 430

Gln Gln Trp Val Ser Glu Thr Cys Phe Pro Ala Gly Thr Leu Ala Lys
        435                 440                 445

Pro Ser Met Lys Asp Leu Glu Tyr Ile Glu Gln Leu Lys Glu Leu Ile
        450                 455                 460

Gln Lys Glu Ala Ile Pro Ala Pro Ser Pro Ile Glu Gln Arg Trp Thr
465                 470                 475                 480

Gly Arg Ser Lys Ser Pro Met Ser Pro Ala Phe Ser Thr Ala Glu Glu
```

-continued

```
                    485                 490                 495
Asp Ile Phe Ser Trp Val Gly Ile Ile Met Tyr Leu Pro Thr Ala Asp
                500                 505                 510

Pro Arg Gln Arg Lys Asp Ile Thr Asp Glu Phe Phe His Tyr Arg His
            515                 520                 525

Leu Thr Gln Ala Lys Leu Trp Asp Gln Tyr Ser Ala Tyr Glu His Trp
        530                 535                 540

Ala Lys Ile Glu Ile Pro Lys Asp Lys Glu Glu Leu Glu Ala Leu Gln
545                 550                 555                 560

Glu Arg Leu Arg Lys Arg Phe Pro Val Asp Ala Tyr Asn Lys Ala Arg
                565                 570                 575

Arg Glu Leu Asp Pro Asn Arg Ile Leu Ser Asn Asn Met Val Glu Lys
            580                 585                 590

Leu Phe Pro Val Ser Lys Thr Ala
        595                 600

<210> SEQ ID NO 4
<211> LENGTH: 2064
<212> TYPE: DNA
<213> ORGANISM: Brassica oleracea

<400> SEQUENCE: 4
aattcggcac gagctttcgc tggctcaggt ttcagatcgc ctgaactaaa acaaaatgct     60
ccgatcactt ctcctccgcc gctccaacgc ccgttcgctt cgaccccccat ttccccctct    120 ccgcactcta tgcacttccg gtcagacctt gactccagcc cctccaccgc cgcctcctcc    180
tccaccgccg atttcatcct ccgcctcaga aaaggagttc cgtaaatacg ccggatacgc    240
agcactcgct ctcttctccg gcgccgcaac ttacttctcc ttccccttcc ccgagaacgc    300
caaacacaag aaggctcaga tcttccgata cgctcctctc cccgaagatc tccacaccgt    360
ctctaactgg agtggtactc acgaggtcca gaccaggaac tttaaccagc cggagactct    420
cgccgatctc gaagctctcg tcaaggaagc tcatgagaag aagaacagga tccgacccgt    480
tggatccggt cttttccccca atgggatcgg tttgtctcgc tcggggatgg tgaatttggc    540
gctcatggac aaggtcctcg aggtggataa agagaagaag agagtccgtg tgcaggctgg    600
gattagggtt cagcagcttg ttgacgccat tcaagagtat ggtctcactc tccagaactt    660
tgcttccatt agagagcagc agattggtgg catcattcag gttggggcac atgggacagg    720
tgctagattg cctcctatcg atgagcaagt gattggcatg aagcttgtca ctcctgctaa    780
gggaactatt gagcttttcta aggataatga tccggagctc tttcatcttg ctcgatgtgg    840
ccttggtgga cttggagttg ttgctgaggt caccctccag tgcgttgaaa gacaggagct    900
tttggagcac acttacgtct ccaccttgga agagatcaag aaaaatcaca aaaagttgct    960
ctctacaaat aagcatgtca gtacctgta tattccatat actgacacgg tcgtggttgt   1020
tacatgcaac cctgtatcaa aatggagtgg ggcacctaag gacaaaccaa gtacactac   1080 agaggaggct ttaaagcatg tccgtgacct gtatagagag agcattgtta agtatagggt   1140
ccaggactct agtaagaaga ctcctgacag tagggagcca gacattaacg agctttcatt   1200
tacagagttg agagataagc tgattgccct agatcctctc aatgacgttc acgttggaaa   1260
agtgaatcaa gctgaggctg agttttggaa aaaatcagaa ggatacagag tagggtggag   1320
tgatgaaatc ctgggctttg actgtggtgg tcaacagtgg gtatcagaaa cttgttttcc   1380
tgctggaact ctcgctaaac ctagcatgaa agaccttgag tacatagaac agctgaaaga   1440
```

-continued

```
gttgatacaa aaagaagcaa taccagcacc ttctcccata gagcagcgtt ggacaggccg    1500
aagtaagagc cctatgagtc ctgcattcag cactgcagag gaggacattt tctcatgggt    1560
tggtataatc atgtatctcc cgacagcaga ccctcgccag agaaaggaca tcacggatga    1620
atttttccac tatagacatt tgacacaggc aaaattgtgg gaccagtatt ctgcgtatga    1680
acattgggct aaaattgaga taccaaagga taaagaggaa cttgaagccc tacaagaaag    1740
actcagaaaa cgattcccgg tggatgcata caacaaagca cgaagggagc tggacccaaa    1800
cagaattctc tcaaacaaca tggtggaaaa gctcttccct gtctccaaga ctgcttaaaa    1860
acattttcat caatagtttt tttgctcctt gaagtaccac ttttggaatc ctataacgtt    1920
gcatctacaa gtgtttgtaa gaagagtgaa gccgatatat tggtcacaaa aaagtttac    1980 attgagtttt actactattt ttttttttcgc agttcccctg aataaatata cttgttgttc    2040
tattccaaaa aaaaaaaaaa aaaa    2064
```

<210> SEQ ID NO 5
<211> LENGTH: 526
<212> TYPE: PRT
<213> ORGANISM: Saccharomyces cerevisiae

<400> SEQUENCE: 5

```
Met Ser Thr Ile Pro Phe Arg Lys Asn Tyr Val Phe Lys Asn Trp Ala
  1               5                  10                  15

Gly Ile Tyr Ser Ala Lys Pro Glu Arg Tyr Phe Gln Pro Ser Ser Ile
             20                  25                  30

Asp Glu Val Val Glu Leu Val Lys Ser Ala Arg Leu Ala Glu Lys Ser
         35                  40                  45

Leu Val Thr Val Gly Ser Gly His Ser Pro Ser Asn Met Cys Val Thr
     50                  55                  60

Asp Glu Trp Leu Val Asn Leu Asp Arg Leu Asp Lys Val Gln Lys Phe
 65                  70                  75                  80

Val Glu Tyr Pro Glu Leu His Tyr Ala Asp Val Thr Val Asp Ala Gly
                 85                  90                  95

Met Arg Leu Tyr Gln Leu Asn Glu Phe Leu Gly Ala Lys Gly Tyr Ser
            100                 105                 110

Ile Gln Asn Leu Gly Ser Ile Ser Glu Gln Ser Val Ala Gly Ile Ile
        115                 120                 125

Ser Thr Gly Ser His Gly Ser Ser Pro Tyr His Gly Leu Ile Ser Ser
    130                 135                 140

Gln Tyr Val Asn Leu Thr Ile Val Asn Gly Lys Gly Glu Leu Lys Phe
145                 150                 155                 160

Leu Asp Ala Glu Asn Asp Pro Glu Val Phe Lys Ala Ala Leu Leu Ser
                165                 170                 175

Val Gly Lys Ile Gly Ile Ile Val Ser Ala Thr Ile Arg Val Val Pro
            180                 185                 190

Gly Phe Asn Ile Lys Ser Thr Gln Glu Val Ile Thr Phe Glu Asn Leu
        195                 200                 205

Leu Lys Gln Trp Asp Thr Leu Trp Thr Ser Ser Glu Phe Ile Arg Val
    210                 215                 220

Trp Trp Tyr Pro Tyr Thr Arg Lys Cys Val Leu Trp Arg Gly Asn Lys
225                 230                 235                 240

Thr Thr Asp Ala Gln Asn Gly Pro Ala Lys Ser Trp Trp Gly Thr Lys
                245                 250                 255

Leu Gly Arg Phe Phe Tyr Glu Thr Leu Leu Trp Ile Ser Thr Lys Ile
```

```
                    260             265             270
Tyr Ala Pro Leu Thr Pro Phe Val Glu Lys Phe Val Phe Asn Arg Gln
            275             280             285

Tyr Gly Lys Leu Glu Lys Ser Ser Thr Gly Asp Val Asn Val Thr Asp
        290             295             300

Ser Ile Ser Gly Phe Asn Met Asp Cys Leu Phe Ser Gln Phe Val Asp
305             310             315             320

Glu Trp Gly Cys Pro Met Asp Asn Gly Leu Glu Val Leu Arg Ser Leu
                325             330             335

Asp His Ser Ile Ala Gln Ala Ala Ile Asn Lys Glu Phe Tyr Val His
            340             345             350

Val Pro Met Glu Val Arg Cys Ser Asn Thr Thr Leu Pro Ser Glu Pro
        355             360             365

Leu Asp Thr Ser Lys Arg Thr Asn Thr Ser Pro Gly Pro Val Tyr Gly
    370             375             380

Asn Val Cys Arg Pro Phe Leu Asp Asn Thr Pro Ser His Cys Arg Phe
385             390             395             400

Ala Pro Leu Glu Asn Val Thr Asn Ser Gln Leu Thr Leu Tyr Ile Asn
                405             410             415

Ala Thr Ile Tyr Arg Pro Phe Gly Cys Asn Thr Pro Ile His Lys Trp
            420             425             430

Phe Thr Leu Phe Glu Asn Thr Met Met Val Ala Gly Gly Lys Pro His
        435             440             445

Trp Ala Lys Asn Phe Leu Gly Ser Thr Thr Leu Ala Ala Gly Pro Val
    450             455             460

Lys Lys Asp Thr Asp Tyr Asp Asp Phe Glu Met Arg Gly Met Ala Leu
465             470             475             480

Lys Val Glu Glu Trp Tyr Gly Glu Asp Leu Lys Lys Phe Arg Lys Ile
                485             490             495

Arg Lys Glu Gln Asp Pro Asp Asn Val Phe Leu Ala Asn Lys Gln Trp
            500             505             510

Ala Ile Ile Asn Gly Ile Ile Asp Pro Ser Glu Leu Ser Asp
        515             520             525

<210> SEQ ID NO 6
<211> LENGTH: 1581
<212> TYPE: DNA
<213> ORGANISM: Saccharomyces cerevisiae

<400> SEQUENCE: 6
atgtctacta tcccatttag aaagaactat gtgttcaaaa actgggccgg aatttattct    60
gcaaaaccag aacgttactt ccaaccaagt tcaattgatg aggttgtcga gttagtaaag   120
agtgccaggc tagctgaaaa agcttagtt actgttggtt cgggccattc tcctagtaac   180
atgtgcgtta ctgatgaatg gcttgttaac ttagacagat tggacaaagt acaaaagttt   240
gttgaatatc ctgagttaca ttatgccgat gtcacagttg atgccggtat gaggctttac   300
caattgaatg aattttggg tgcgaaaggt tactctatcc aaaatttagg ctctatctca   360
gaacaaagtg ttgctggcat aatctctact ggtagtcatg gttcctcacc ttatcacggt   420
ttgatttctt ctcaatacgt aaacttgact attgttaatg gtaagggcga attgaagttc   480
ttggatgccg aaaacgatcc agaagtcttt aaagctgctt tactttcagt tggaaaaatt   540
ggtatcattg tctctgctac tatcagggtt gttcccggct tcaatattaa atccactcaa   600
gaagtgatta cttttgaaaa cctttttgaag caatgggata cccctatggac ttcatctgaa   660
```

```
tttatcagag tttggtggta cccttatact agaaaatgtg ttctatggag gggtaacaaa    720
actacagatg cccaaaatgg tccagccaag tcatggtggg gtaccaagct gggtagattt    780
ttctacgaaa ctctattatg gatctctacc aaaatctatg cgccattaac cccatttgtg    840
gaaaagttcg ttttcaacag gcaatatggg aaattggaga agagctctac tggtgatgtt    900
aatgttaccg attctatcag cggatttaat atggactgtt tgttttcaca atttgttgat    960 gaatggggt gccctatgga taatggtttg gaagtcttac gttcattgga tcattctatt   1020
gcgcaggctg ccataaacaa agaatttat gtccacgtgc ctatggaagt ccgttgctca   1080
aatactacat taccttctga acccttggat actagcaaga gaacaaacac cagtcccggt   1140
cccgtttatg gcaatgtgtg ccgcccattc ctggataaca caccatccca ttgcagattt   1200
gctccgttgg aaaatgttac caacagtcag ttgacgttgt acataaatgc taccatttat   1260
aggccgtttg gctgtaatac tccaattcat aaatggttta ccctttttga aaatactatg   1320
atggtagcgg gaggtaagcc acattgggcc aagaacttcc taggctcaac cactctagct   1380
gctggaccag tgaaaaagga tactgattac gatgactttg aaatgagggg gatggcattg   1440
aaggttgaag aatggtatgg cgaggatttg aaaaagttcc ggaaaataag aaaggagcaa   1500
gatcccgata atgtattctt ggcaaacaaa cagtgggcta tcataaatgg tattatagat   1560
cctagtgagt tgtccgacta g                                             1581

<210> SEQ ID NO 7
<211> LENGTH: 526
<212> TYPE: PRT
<213> ORGANISM: Saccharomyces cerevisiae

<400> SEQUENCE: 7

Met Ser Thr Ile Pro Phe Arg Lys Asn Tyr Val Phe Lys Asn Trp Ala
  1               5                  10                  15

Gly Ile Tyr Ser Ala Lys Pro Glu Arg Tyr Phe Gln Pro Ser Ser Ile
                 20                  25                  30

Asp Glu Val Val Glu Leu Val Lys Ser Ala Arg Leu Ala Glu Lys Ser
             35                  40                  45

Leu Val Thr Val Gly Ser Gly His Ser Pro Ser Asn Met Cys Val Thr
         50                  55                  60

Asp Glu Trp Leu Val Asn Leu Asp Arg Leu Asp Lys Val Gln Lys Phe
 65                  70                  75                  80

Val Glu Tyr Pro Glu Leu His Tyr Ala Asp Val Thr Val Asp Ala Gly
                 85                  90                  95

Met Arg Leu Tyr Gln Leu Asn Glu Phe Leu Gly Ala Lys Gly Tyr Ser
                100                 105                 110

Ile Gln Asn Leu Gly Ser Ile Ser Glu Gln Ser Val Ala Gly Ile Ile
            115                 120                 125

Ser Thr Gly Ser His Gly Ser Ser Pro Tyr His Gly Leu Ile Ser Ser
        130                 135                 140

Gln Tyr Val Asn Leu Thr Ile Val Asn Gly Lys Gly Glu Leu Lys Phe
145                 150                 155                 160

Leu Asp Ala Glu Asn Asp Pro Glu Val Phe Lys Ala Ala Leu Leu Ser
                165                 170                 175

Val Gly Lys Ile Gly Ile Ile Val Ser Ala Thr Ile Arg Val Val Pro
            180                 185                 190

Gly Phe Asn Ile Lys Ser Thr Gln Glu Val Ile Thr Phe Glu Asn Leu
        195                 200                 205
```

```
Leu Lys Gln Trp Asp Thr Leu Trp Thr Ser Glu Phe Ile Arg Val
    210                 215                 220

Trp Trp Tyr Pro Tyr Thr Arg Lys Cys Val Leu Trp Arg Gly Asn Lys
225                 230                 235                 240

Thr Thr Asp Ala Gln Asn Gly Pro Ala Lys Ser Trp Trp Gly Thr Lys
                245                 250                 255

Leu Gly Arg Phe Phe Tyr Glu Thr Leu Leu Trp Ile Ser Thr Lys Ile
                260                 265                 270

Tyr Ala Pro Leu Thr Pro Phe Val Glu Lys Phe Val Phe Asn Arg Gln
            275                 280                 285

Tyr Gly Lys Leu Glu Lys Ser Ser Thr Gly Asp Val Asn Val Thr Asp
        290                 295                 300

Ser Ile Ser Gly Phe Asn Met Asp Cys Leu Phe Ser Gln Phe Val Asp
305                 310                 315                 320

Glu Trp Gly Cys Pro Met Asp Asn Gly Leu Glu Val Leu Arg Ser Leu
                325                 330                 335

Asp His Ser Ile Ala Gln Ala Ala Ile Asn Lys Glu Phe Tyr Val His
                340                 345                 350

Val Pro Met Glu Val Arg Cys Ser Asn Thr Thr Leu Pro Ser Glu Pro
            355                 360                 365

Leu Asp Thr Ser Lys Arg Thr Asn Thr Ser Pro Gly Pro Val Tyr Gly
        370                 375                 380

Asn Val Cys Arg Pro Phe Leu Asp Asn Thr Pro Ser His Cys Arg Phe
385                 390                 395                 400

Ala Pro Leu Glu Asn Val Thr Asn Ser Gln Leu Thr Leu Tyr Ile Asn
                405                 410                 415

Pro Thr Ile Tyr Arg Pro Phe Gly Cys Asn Thr Pro Ile His Lys Trp
            420                 425                 430

Phe Thr Leu Phe Glu Asn Thr Met Met Val Ala Gly Lys Pro His
        435                 440                 445

Trp Ala Lys Asn Phe Leu Gly Ser Thr Thr Leu Ala Ala Gly Pro Val
    450                 455                 460

Lys Lys Asp Thr Asp Tyr Asp Asp Phe Glu Met Arg Gly Met Ala Leu
465                 470                 475                 480

Lys Val Glu Glu Trp Tyr Gly Glu Asp Leu Lys Lys Phe Arg Lys Ile
                485                 490                 495

Arg Lys Glu Gln Asp Pro Asp Asn Val Phe Leu Ala Asn Lys Gln Trp
            500                 505                 510

Ala Ile Ile Asn Gly Ile Ile Asp Pro Ser Glu Leu Ser Asp
        515                 520                 525
```

<210> SEQ ID NO 8
<211> LENGTH: 2138
<212> TYPE: DNA
<213> ORGANISM: Saccharomyces cerevisiae

<400> SEQUENCE: 8

| | | | | | |
|---|---|---|---|---|---|
| cccatgtcta | ctatcccatt | tagaaagaac | tatgtgttca | aaaactgggc | cggaatttat | 60 |
| tctgcaaaac | cagaacgtta | cttccaacca | agttcaattg | atgaggttgt | cgagttagta | 120 |
| aagagtgcca | ggctagctga | aaaagctta | gttactgttg | gttcgggcca | ttctcctagt | 180 |
| aacatgtgcg | ttactgatga | atggcttgtt | aacttagaca | gattggacaa | agtacaaaag | 240 |
| tttgttgaat | atcctgagtt | acattatgcc | gatgtcacag | ttgatgccgg | tatgaggctt | 300 |

-continued

| | |
|---|---|
| taccaattga atgaattttt gggtgcgaaa ggttactcta tccaaaattt aggctctatc | 360 |
| tcagaacaaa gtgttgctgg cataatctct actggtagtc atggttcctc accttatcac | 420 |
| ggtttgattt cttctcaata cgtaaacttg actattgtta atggtaaggg cgaattgaag | 480 |
| ttcttggatg ccgaaaacga tccagaagtc tttaaagctg ctttactttc agttggaaaa | 540 |
| atcggtatca ttgtctctgc tactatcagg gttgttcccg gcttcaatat taaatccact | 600 |
| caagaagtga ttacttttga aaaccttttg aagcaatggg atacccctatg gacttcatct | 660 |
| gaatttatca gagtttggtg gtacccttat actagaaaat gtgttctatg gaggggtaac | 720 |
| aaaactacag atgcccaaaa tggtccagcc aagtcatggt ggggtaccaa gctgggtaga | 780 |
| tttttctacg aaactctatt atggatctct accaaaatct atgcgccatt aaccccattt | 840 |
| gtggaaaagt tcgttttcaa caggcaatac gggaaattgg agaagagctc tactggtgat | 900 |
| gttaatgtta ccgattctat cagcggattt aatatggact gtttgttttc acaatttgtt | 960 |
| gatgaatggg ggtgccctat ggataatggt ttggaagtct tacgttcatt ggatcattct | 1020 |
| attgcgcagg ctgccataaa caagaattt tatgtccacg tgcctatgga agtccgttgc | 1080 |
| tcaaatacta cattaccttc tgaacccttg gatactagca agagaacaaa caccagtccc | 1140 |
| ggtcccgttt atggcaatgt gtgccgccca ttcctggata cacaccatc ccattgcaga | 1200 |
| tttgctccgt tggaaaatgt taccaacagt cagttgacgt tgtacataaa tcctaccatt | 1260 |
| tataggccgt ttggctgtaa tactccaatt cataaatggt ttacccttttt tgaaaatact | 1320 |
| atgatggtag cggaggtaa gccacattgg gccaagaact tcctaggctc aaccactcta | 1380 |
| gctgctggac cagtgaaaaa ggatactgat tacgatgact ttgaaatgag ggggatggca | 1440 |
| ttgaaggttg aagaatggta tggcgaggat ttgaaaagt tccggaaaat aagaaaggag | 1500 |
| caagatcccg ataatgtatt cttggcaaac aaacagtggg ctatcataaa tggtattata | 1560 |
| gatcctagtg agttgtccga ctagtctctt tttgtctcaa taatctctat attttactaa | 1620 |
| aaaagaatat atatatatat atttatatat agcagtgtga tgactgttca tgtacattct | 1680 |
| aataactatt cctagctgcc tatcaaagac ttttttttga attagagctt tttagtaatc | 1740 |
| atgggaccct tttttctttt cattatcctt actatagttt ttttttggaa aagccgaacg | 1800 |
| cggtaatgat tggtcgtata agcaaaaacg aaacatcggc atggcataac gtagatccta | 1860 |
| tctacaggga agtttttaga aatcagatag aaatgtattt tgagtgctgt atatattgca | 1920 |
| gtacttttttt tctctctagg atttaagtat gtttagtatt aactcatatc acatttttc | 1980 |
| tttgtaaaaa gcaaccattc gcaacaatgt cgatagtaga gacatgcata tcgtttgttt | 2040 |
| cgacaaatcc gtttatcca ttttgtactg gattgcttct gaattgtgtg gttacaccgc | 2100 |
| tttacttttg gaaaacgcaa aatggtagaa tcgtggtc | 2138 |

<210> SEQ ID NO 9
<211> LENGTH: 440
<212> TYPE: PRT
<213> ORGANISM: Rattus norvegicus

<400> SEQUENCE: 9

Met Val His Gly Tyr Lys Gly Val Gln Phe Gln Asn Trp Ala Lys Thr
 1               5                  10                  15

Tyr Gly Cys Ser Pro Glu Val Tyr Tyr Gln Pro Thr Ser Val Glu Glu
            20                  25                  30

Val Arg Glu Val Leu Ala Leu Ala Arg Glu Gln Lys Lys Lys Val Lys
        35                  40                  45

-continued

```
Val Val Gly Gly Gly His Ser Pro Ser Asp Ile Ala Cys Thr Asp Gly
 50                  55                  60

Phe Met Ile His Met Gly Lys Met Asn Arg Val Leu Gln Val Asp Lys
 65                  70                  75                  80

Glu Lys Lys Gln Ile Thr Val Glu Ala Gly Ile Leu Leu Ala Asp Leu
                 85                  90                  95

His Pro Gln Leu Asp Glu His Gly Leu Ala Met Ser Asn Leu Gly Ala
                100                 105                 110

Val Ser Asp Val Thr Val Ala Gly Val Ile Gly Ser Gly Thr His Asn
                115                 120                 125

Thr Gly Ile Lys His Gly Ile Leu Ala Thr Gln Val Ala Leu Thr
130                 135                 140

Leu Met Thr Ala Asp Gly Glu Val Leu Glu Cys Ser Glu Ser Arg Asn
145                 150                 155                 160

Ala Asp Val Phe Gln Ala Ala Arg Val His Leu Gly Cys Leu Gly Ile
                165                 170                 175

Ile Leu Thr Val Thr Leu Gln Cys Val Pro Gln Phe Gln Leu Gln Glu
                180                 185                 190

Thr Ser Phe Pro Ser Thr Leu Lys Glu Val Leu Asp Asn Leu Asp Ser
                195                 200                 205

His Leu Lys Arg Ser Glu Tyr Phe Arg Phe Leu Trp Phe Pro His Thr
                210                 215                 220

Glu Asn Val Ser Ile Ile Tyr Gln Asp His Thr Asn Lys Ala Pro Ser
225                 230                 235                 240

Ser Ala Ser Asn Trp Phe Trp Asp Tyr Ala Ile Gly Phe Tyr Leu Leu
                245                 250                 255

Glu Phe Leu Leu Trp Thr Ser Thr Tyr Leu Pro Cys Leu Val Gly Trp
                260                 265                 270

Ile Asn Arg Phe Phe Phe Trp Met Leu Phe Asn Cys Lys Lys Glu Ser
                275                 280                 285

Ser Asn Leu Ser His Lys Ile Phe Thr Tyr Glu Cys Arg Phe Lys Gln
                290                 295                 300

His Val Gln Asp Trp Ala Ile Pro Arg Glu Lys Thr Lys Glu Ala Leu
305                 310                 315                 320

Leu Glu Leu Lys Ala Met Leu Glu Ala His Pro Lys Val Val Ala His
                325                 330                 335

Tyr Pro Val Glu Val Arg Phe Thr Arg Gly Asp Asp Ile Leu Leu Ser
                340                 345                 350

Pro Cys Phe Gln Arg Asp Ser Cys Tyr Met Asn Ile Ile Met Tyr Arg
                355                 360                 365

Pro Tyr Gly Lys Asp Val Pro Arg Leu Asp Tyr Trp Leu Ala Tyr Glu
                370                 375                 380

Thr Ile Met Lys Lys Phe Gly Gly Arg Pro His Trp Ala Lys Ala His
385                 390                 395                 400

Asn Cys Thr Gln Lys Asp Phe Glu Glu Met Tyr Pro Thr Phe His Lys
                405                 410                 415

Phe Cys Asp Ile Arg Glu Lys Leu Asp Pro Thr Gly Met Phe Leu Asn
                420                 425                 430

Ser Tyr Leu Glu Lys Val Phe Tyr
                435                 440

<210> SEQ ID NO 10
<211> LENGTH: 2120
<212> TYPE: DNA
```

<210> ORGANISM: Rattus norvegicus

<400> SEQUENCE: 10

| | | | | | |
|---|---|---|---|---|---|
| ggatcctcct | gatcactgga | atcatggtcc | atgggtacaa | aggggtccag | ttccaaaatt | 60 |
| gggcaaagac | ctatggttgc | agtccagagg | tgtactacca | gcccacctcc | gtggaggagg | 120 |
| tcagagaggt | gctggccctg | gcccgggagc | agaagaagaa | agtgaaggtg | gtgggtggtg | 180 |
| gccactcgcc | ttcagacatt | gcctgcactg | acggtttcat | gatccacatg | ggcaagatga | 240 |
| accgggttct | ccaggtggac | aaggagaaga | agcagataac | agtggaagcc | ggtatcctcc | 300 |
| tggctgacct | gcacccacag | ctggatgagc | atggcctggc | catgtccaat | ctgggagcag | 360 |
| tgtctgatgt | gacagttgct | ggtgtcattg | gatccggaac | acataacaca | gggatcaagc | 420 |
| acggcatcct | ggccactcag | gtggtggccc | tgaccctgat | gacagctgat | ggagaagttc | 480 |
| tggaatgttc | tgagtcaaga | aatgcagatg | tgttccaggc | tgcacgggtg | cacctggggtt | 540 |
| gcctgggcat | catcctcacc | gtcaccctgc | agtgtgtgcc | tcagtttcag | cttcaggaga | 600 |
| catccttccc | ttcgaccctc | aaagaggtcc | ttgacaacct | agacagccac | ctgaagaggt | 660 |
| ctgagtactt | ccgcttcctc | tggtttcctc | acactgagaa | cgtcagcatc | atctaccaag | 720 |
| accacaccaa | caaggccccc | tcctctgcat | ctaactggtt | tgggactat | gccatcgggt | 780 |
| tctacctact | ggagttcttg | ctctggacca | gcacctacct | gccatgcctc | gtgggctgga | 840 |
| tcaaccgctt | cttcttctgg | atgctgttca | actgcaagaa | ggagagcagc | aacctcagtc | 900 |
| acaagatctt | cacctacgag | tgtcgcttca | agcagcatgt | acaagactgg | gccatcccta | 960 |
| gggagaagac | caaggaggcc | ctactggagc | taaaggccat | gctggaggcc | caccccaaag | 1020 |
| tggtagccca | ctaccccgta | gaggtgcgct | tcacccgagg | cgatgacatt | ctgctgagcc | 1080 |
| cctgcttcca | gagggacagc | tgctacatga | acatcattat | gtacaggccc | tatggaaagg | 1140 |
| acgtgcctcg | gctagactac | tggctggcct | atgagaccac | catgaagaag | tttgaggaa | 1200 |
| gaccccactg | ggcaaaggcc | cacaattgca | cccagaagga | ctttgaggaa | atgtacccca | 1260 |
| cctttcacaa | gttctgtgac | atccgtgaga | agctggaccc | cactgaaatg | ttcttgaatt | 1320 |
| cgtacctgga | gaaagtcttc | tactaaagca | ggagtggaaa | caaaccaccc | tgaccccctca | 1380 |
| cacttctgct | gccccgggg | gtctggggag | cagagaagtg | cctcacaagc | acaatgggaa | 1440 |
| ctgacctctc | ctcctgacca | caagaaagg | ctgggctctg | ggccgggtcc | tctctgcctt | 1500 |
| cggcatcatt | tcccttacat | ccaggcgaag | aagtggcctc | tcactcaaat | tcctgttagc | 1560 |
| atttccatgg | gtcacacata | aactgcaatc | ctctcaggag | aaggggatc | cctgatacat | 1620 |
| catatctatc | cagactaagg | atgtggttct | tcctagattc | tatggctcca | ccaggtatag | 1680 |
| agagattcct | ggggcctgca | gttctccatc | cctcttcaga | agggagggat | cccttggcga | 1740 |
| gagtttggct | cagaggtggc | atgaagcatg | ctctgctctc | tcttacccctt | gaaggtcctt | 1800 |
| cggatgccca | gagatgtctg | ctggtcctgg | gcaagccatc | attcaaacgg | tccaacctg | 1860 |
| gccttctgtc | tgccatggcc | tgaccctcgc | agtgtctctt | ccagaggtgt | ttagagtgga | 1920 |
| actcgcttca | acctcttaac | cagttgctga | tccctgtgtt | tctctcccttt | ctccttggag | 1980 |
| actactcttg | gaggggatc | ccaccatgtc | cttggctttc | cctgggtatt | gttctcctct | 2040 |
| tcctcttcac | aaatatgatt | tcagtttgat | ttgtggcctt | tctggagtgt | tccttggaga | 2100 |
| accaagatgt | tccagctacc | | | | | 2120 |

<210> SEQ ID NO 11
<211> LENGTH: 319

```
<212> TYPE: PRT
<213> ORGANISM: Arabidopsis thaliana

<400> SEQUENCE: 11

Met Thr Lys Ile Glu Leu Arg Ala Leu Gly Asn Thr Gly Leu Lys Val
  1               5                  10                  15

Ser Ala Val Gly Phe Gly Ala Ser Pro Leu Gly Ser Val Phe Gly Pro
             20                  25                  30

Val Ala Glu Asp Ala Val Ala Thr Val Arg Glu Ala Phe Arg Leu
         35                  40                  45

Gly Ile Asn Phe Phe Asp Thr Ser Pro Tyr Tyr Gly Gly Thr Leu Ser
         50                  55                  60

Glu Lys Met Leu Gly Lys Gly Leu Lys Ala Leu Gln Val Pro Arg Ser
 65                  70                  75                  80

Asp Tyr Ile Val Ala Thr Lys Cys Gly Arg Tyr Lys Glu Gly Phe Asp
                 85                  90                  95

Phe Ser Ala Glu Arg Val Arg Lys Ser Ile Asp Glu Ser Leu Glu Arg
                100                 105                 110

Leu Gln Leu Asp Tyr Val Asp Ile Leu His Cys His Asp Ile Glu Phe
            115                 120                 125

Gly Ser Leu Asp Gln Ile Val Ser Glu Thr Ile Pro Ala Leu Gln Lys
130                 135                 140

Leu Lys Gln Glu Gly Lys Thr Arg Phe Ile Gly Ile Thr Gly Leu Pro
145                 150                 155                 160

Leu Asp Ile Phe Thr Tyr Val Leu Asp Arg Val Pro Pro Gly Thr Val
                165                 170                 175

Asp Val Ile Leu Ser Tyr Cys His Tyr Gly Val Asn Asp Ser Thr Leu
            180                 185                 190

Leu Asp Leu Leu Pro Tyr Leu Lys Ser Lys Gly Val Gly Val Ile Ser
            195                 200                 205

Ala Ser Pro Leu Ala Met Gly Leu Leu Thr Glu Gln Gly Pro Pro Glu
210                 215                 220

Trp His Pro Ala Ser Pro Glu Leu Lys Ser Ala Ser Lys Ala Ala Val
225                 230                 235                 240

Ala His Cys Lys Ser Lys Gly Lys Lys Ile Thr Lys Leu Ala Leu Gln
                245                 250                 255

Tyr Ser Leu Ala Asn Lys Glu Ile Ser Ser Val Leu Val Gly Met Ser
            260                 265                 270

Ser Val Ser Gln Val Glu Glu Asn Val Ala Ala Val Thr Glu Leu Glu
        275                 280                 285

Ser Leu Gly Met Asp Gln Glu Thr Leu Ser Glu Val Glu Ala Ile Leu
    290                 295                 300

Glu Pro Val Lys Asn Leu Thr Trp Pro Ser Gly Ile His Gln Asn
305                 310                 315

<210> SEQ ID NO 12
<211> LENGTH: 960
<212> TYPE: DNA
<213> ORGANISM: Arabidopsis thaliana

<400> SEQUENCE: 12
atgacgaaaa tagagcttcg agctttgggg aacacagggc ttaaggttag cgccgttggt      60
tttggtgcct ctccgctcgg aagtgtcttc ggtccagtcg ccgaagatga tgccgtcgcc     120
accgtgcgcg aggctttccg tctcggtatc aacttcttcg acacctcccc gtattatgga     180
```

```
ggaacactgt ctgagaaaat gcttggtaag ggactaaagg cttgcaagt ccctagaagt    240 gactacattg tggctactaa gtgtggtaga tataaagaag gttttgattt cagtgctgag    300
agagtaagaa agagtattga cgagagcttg gagaggcttc agcttgatta tgttgacata    360
cttcattgcc atgacattga gttcgggtct cttgatcaga ttgtgagtga acaattcct    420 gctcttcaga aactgaaaca agaggggaag acccggttca ttggtatcac tggtcttccg    480
ttagatattt tcacttatgt tcttgatcga gtgcctccag ggactgtcga tgtgatattg    540
tcatactgtc attacggcgt taatgattcg acgttgctgg atttactacc ttacttgaag    600
agcaaaggtg tgggtgtgat aagtgcttct ccattagcaa tgggcctcct tacagaacaa    660
ggtcctcctg aatggcaccc tgcttcccct gagctcaagt ctgcaagcaa agccgcagtt    720
gctcactgca atcaaaggg caagaagatc acaaagttag ctctgcaata cagtttagca    780
aacaaggaga tttcgtcggt gttggttggg atgagctctg tctcacaggt agaagaaaat    840
gttgcagcag ttacagagct tgaaagtctg gggatggatc aagaaactct gtctgaggtt    900
gaagctattc tcgagcctgt aaagaatctg acatggccaa gtggaatcca tcagaactaa    960
```

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: motif I of
      aldo-keto reductase superfamily
<221> NAME/KEY: VARIANT
<222> LOCATION: (2)
<223> OTHER INFORMATION: Xaa = any amino acid
<221> NAME/KEY: VARIANT
<222> LOCATION: (4)..(5)
<223> OTHER INFORMATION: Xaa = any amino acid
<221> NAME/KEY: VARIANT
<222> LOCATION: (7)
<223> OTHER INFORMATION: Xaa = any amino acid
<221> NAME/KEY: VARIANT
<222> LOCATION: (9)..(13)
<223> OTHER INFORMATION: Xaa = any amino acid
<221> NAME/KEY: VARIANT
<222> LOCATION: (15)..(17)
<223> OTHER INFORMATION: Xaa = any amino acid

<400> SEQUENCE: 13

Gly Xaa Arg Xaa Xaa Asp Xaa Ala Xaa Xaa Xaa Xaa Xaa Glu Xaa Xaa
 1               5                  10                  15

Xaa Gly

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Forward PCR
      Primer for L-galactono-1,4-lactone dehydrogenase
      from A. thaliana

<400> SEQUENCE: 14
caagaaggcc taaatgttcc gttacgctcc                                      30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Reverse PCR
      Primer for L-galactono-1,4-lactone dehydrogenase from A. thaliana

<400> SEQUENCE: 15
atgggccctt aagcagtggt ggagactggg                                                30

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Forward PCR
      Primer for L-gulono-1,4-lactone oxidase from R.
      norvegicus

<400> SEQUENCE: 16 tgagggtca gggtggtttg tttcca                                                    26

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Reverse PCR
      Primer for L-gulono-1,4-lactone oxidase from R.
      norvegicus

<400> SEQUENCE: 17
tggaatcatg gtccatgggt acaaaggg                                                 28

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Forward PCR
      Primer for D-arabinono-1,4-lactone oxidase from S.
      cerevisiae

<400> SEQUENCE: 18
tttcaccata tgtctactat cc                                                       22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Reverse PCR
      Primer for D-arabinono-1,4-lactone oxidase from S.
      cerevisiae

<400> SEQUENCE: 19
aaggatccta gtcggacaac tc                                                       22

<210> SEQ ID NO 20
<211> LENGTH: 344
<212> TYPE: PRT
<213> ORGANISM: Saccharomyces cerevisiae

<400> SEQUENCE: 20

Met Ser Ser Ser Val Ala Ser Thr Glu Asn Ile Val Glu Asn Met Leu
  1               5                  10                  15

His Pro Lys Thr Thr Glu Ile Tyr Phe Ser Leu Asn Asn Gly Val Arg
             20                  25                  30

Ile Pro Ala Leu Gly Leu Gly Thr Ala Asn Pro His Glu Lys Leu Ala
         35                  40                  45

```
Glu Thr Lys Gln Ala Val Lys Ala Ala Ile Lys Ala Gly Tyr Arg His
 50                  55                  60

Ile Asp Thr Ala Trp Ala Tyr Glu Thr Glu Pro Phe Val Gly Glu Ala
 65                  70                  75                  80

Ile Lys Glu Leu Leu Glu Asp Gly Ser Ile Lys Arg Glu Asp Leu Phe
                 85                  90                  95

Ile Thr Thr Lys Val Trp Pro Val Leu Trp Asp Glu Val Asp Arg Ser
            100                 105                 110

Leu Asn Glu Ser Leu Lys Ala Leu Gly Leu Glu Tyr Val Asp Leu Leu
            115                 120                 125

Leu Gln His Trp Pro Leu Cys Phe Glu Lys Ile Lys Asp Pro Lys Gly
130                 135                 140

Ile Ser Gly Leu Val Lys Thr Pro Val Asp Asp Ser Gly Lys Thr Met
145                 150                 155                 160

Tyr Ala Ala Asp Gly Asp Tyr Leu Glu Thr Tyr Lys Gln Leu Glu Lys
                165                 170                 175

Ile Tyr Leu Asp Pro Asn Asp His Arg Val Arg Ala Ile Gly Val Ser
            180                 185                 190

Asn Phe Ser Ile Glu Tyr Leu Glu Arg Leu Ile Lys Glu Cys Arg Val
            195                 200                 205

Lys Pro Thr Val Asn Gln Val Glu Thr His Pro His Leu Pro Gln Met
210                 215                 220

Glu Leu Arg Lys Phe Cys Phe Met His Asp Ile Leu Leu Thr Ala Tyr
225                 230                 235                 240

Ser Pro Leu Gly Ser His Gly Ala Pro Asn Leu Lys Ile Pro Leu Val
                245                 250                 255

Lys Lys Leu Ala Glu Lys Tyr Asn Val Thr Gly Asn Asp Leu Leu Ile
            260                 265                 270

Ser Tyr His Ile Arg Gln Gly Thr Ile Val Ile Pro Arg Ser Leu Asn
            275                 280                 285

Pro Val Arg Ile Ser Ser Ser Ile Glu Phe Ala Ser Leu Thr Lys Asp
290                 295                 300

Glu Leu Gln Glu Leu Asn Asp Phe Gly Glu Lys Tyr Pro Val Arg Phe
305                 310                 315                 320

Ile Asp Glu Pro Phe Ala Ala Ile Leu Pro Glu Phe Thr Gly Asn Gly
                325                 330                 335

Pro Asn Leu Asp Asn Leu Lys Tyr
            340

<210> SEQ ID NO 21
<211> LENGTH: 1509
<212> TYPE: DNA
<213> ORGANISM: Saccharomyces cerevisiae

<400> SEQUENCE: 21
taacaatttc gtttactgaa atgctacta gtatataatc attaagtatc taactatcac      60
tcaataaaaa tattatagat cgcttaaaaa ctcgtttatt gccgattata aatccaccaa    120
aagccgctct acccttacct ccgcctggaa aaattataat atataaagtg agcctcgtaa    180 tacagggta aaaggaaag aggggatat caagcatctg gacttatttg cactatctcc      240
gccttcaatt gataaaagcg tcttgattt aatcaactgc tatcatgtct tcttcagtag    300
cctcaaccga aacatagtc gaaaatatgt tgcatccaaa gactacagaa atatactttt    360
cactcaacaa tggtgttcgt atcccagcac tgggtttggg gacagcaaat cctcacgaaa    420
```

-continued

```
agttagctga acaaaacaa gccgtaaaag ctgcaatcaa agctggatac aggcacattg    480
atactgcttg ggcctacgag acagagccat tcgtaggtga agccatcaag gagttattag    540
aagatggatc tatcaaaagg gaggatcttt tcataaccac aaaagtgtgg ccggttctat    600
gggacgaagt ggacagatca ttgaatgaat ctttgaaagc tttaggcttg gaatacgtcg    660
acttgctctt gcaacattgg ccgctatgtt ttgaaaagat taaggaccct aagggatca    720 gcggactggt gaagactccg gttgatgatt ctggaaaaac aatgtatgct gccgacggtg    780
actatttaga aacttacaag caattggaaa aaatttacct tgatcctaac gatcatcgtg    840
tgagagccat tggtgtctca aattttttcca ttgagtattt ggaacgtctc attaaggaat    900
gcagagttaa gccaacggtg aaccaagtgg aaactcaccc tcacttacca caaatggaac    960
taagaaagtt ctgctttatg cacgacattc tgttaacagc atactcacca ttaggttccc    1020
atggcgcacc aaacttgaaa atcccactag tgaaaaagct tgccgaaaag tacaatgtca    1080
caggaaatga cttgctaatt tcttaccata ttagacaagg cactatcgta attccgagat    1140
ccttgaatcc agttaggatt tcctcgagta ttgaattcgc atctttgaca aaggatgaat    1200
tacaagagtt gaacgacttc ggtgaaaaat acccagtgag attcatcgat gagccatttg    1260
cagccatcct tccagagttt actggtaacg gaccaaactt ggacaattta agtattaag    1320 acaacgactt tatttttcact ttatttagtt cgcttcttaa tcttgtcaaa aacaagatat    1380
tgtgtaatcg cctcaagtaa acaatatgtt tttcatacgt gatttgaagt ttttaagtat    1440
ctgaaataca tacgcgcgcg tatgcatatg tattagttaa attactcgaa tgtcctttat    1500
ataatatta                                                              1509
```

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Forward PCR
      Primer for L-galactose dehydrogenase from A.
      thaliana

<400> SEQUENCE: 22
atgacgaaaa tagagcttcg agc                                              23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Reverse PCR
      Primer for L-galactose dehydrogenase from A.
      thaliana

<400> SEQUENCE: 23
ttagttctga tggattccac ttgg                                             24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence:
      Saccharomyces cerevisiae

<400> SEQUENCE: 24
atgtcttctt cagtagcctc aacc                                             24

```
<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Reverse PCR
      Primer for D-arabinose dehydrogenase from  S.
      cerevisiae

<400> SEQUENCE: 25
ttaatacttt aaattgtcca agtttggtc                                       29

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: motif II of
      aldo-keto reductase superfamily
<221> NAME/KEY: VARIANT
<222> LOCATION: (2)..(3)
<223> OTHER INFORMATION: Xaa = any amino acid

<400> SEQUENCE: 26

Gly Xaa Xaa Asn
 1
```

ASCORBIC ACID PRODUCTION FROM YEAST

BACKGROUND OF THE INVENTION

1. Field of the Invention

The present invention relates generally to the field of ascorbic acid production. More particularly, it relates to a process for the production of L-ascorbic acid from yeast, including recombinant yeast.

2. Description of Related Art

L-ascorbic acid (Vitamin C) is a powerful water-soluble antioxidant that is vital for growth and maintenance of all tissue types in humans. One important role of ascorbic acid is its involvement in the production of collagen, an essential cellular component for connective tissues, muscles, tendons, bones, teeth and skin. Collagen is also required for the repair of blood vessels, bruises, and broken bones. Ascorbic acid helps regulate blood pressure, contributes to reduced cholesterol levels, and aids in the removal of cholesterol deposits from arterial walls. Ascorbic acid also aids in the metabolization of folic acid, regulates the uptake of iron, and is required for the conversion of the amino acids L-tyrosine and L-phenylalanine into noradrenaline. The conversion of tryptophan into seratonin, the neurohormone responsible for sleep, pain control, and well-being, also requires adequate supplies of ascorbic acid.

A deficiency of L-ascorbic acid can impair the production of collagen and lead to joint pain, anemia, nervousness and retarded growth. Other effects are reduced immune response and increased susceptibility to infections. The most extreme form of ascorbic acid deficiency is scurvy, a condition evidenced by swelling of the joints, bleeding gums, and the hemorrhaging of capillaries below the surface of the skin. If left untreated, scurvy is fatal.

Although intestines easily absorb ascorbic acid, it is excreted to the urine within two to four hours of ingestion. Therefore, it cannot be stored in the body. L-ascorbic acid is produced in all higher plants and in the liver or kidney of most higher animals, but not humans, bats, some birds and a variety of fishes. Therefore, humans must have access to sufficient amounts of ascorbic acid from adequate dietary sources or supplements in order to maintain optimal health.

Food sources of ascorbic acid include citrus fruits, potatoes, peppers, green leafy vegetables, tomatoes, and berries. Ascorbic acid is also commercially available as a supplement in forms such as pills, tablets, powders, wafers, and syrups.

L-Ascorbic acid is approved for use as a dietary supplement and chemical preservative by the U.S. Food and Drug Administration and is on the FDA's list of substances generally recognized as safe. L-Ascorbic acid may be used in soft drinks as an antioxidant for flavor ingredients, in meat and meat-containing products, for curing and pickling, in flour to improve baking quality, in beer as a stabilizer, in fats and oils as an antioxidant, and in a wide variety of foods for ascorbic acid enrichment. L-Ascorbic acid may also find use in stain removers, hair-care products, plastics manufacture, photography, and water treatment.

The enzymes of the biosynthetic pathways leading to ascorbic acid have not been identified yet to completion. Current understanding of the physiological pathways in plants and animals is shown in FIG. 1.

In animals, D-glucose serves as the first precursor and the last step is catalyzed by a microsomal L-gulono-1,4-lactone oxidase. The enzyme has been isolated and characterized from different sources. The gene from rat has been cloned and sequenced (Koshizaka T. et al., 1998, J. Biol. Chem. 263, 1619–1621.)

Two discrete pathways have been reported for ascorbic acid synthesis in plants. In one pathway, L-ascorbic acid is synthesized from D-glucose via L-sorbosone (Loewus M. W. et al., 1990, Plant. Physiol. 94, 1492–1495). Current evidence suggests that the main physiological pathway proceeds from D-glucose via L-galactose and L-galactono-1,4-lactone to L-ascorbic acid (Wheeler G. L. et al. 1998, Nature, 393, 365–369,). The last two steps are catalyzed by the enzymes L-galactose dehydrogenase and L-galactono-1,4-lactone dehydrogenase. Also in this case, the last enzyme has been isolated and characterized, and the gene from *Brassica oleracea* has been cloned and sequenced (Østergaard J. et al. 1997, J. Biol. Chem., 272, 30009–30016).

For use as a dietary supplement, ascorbic acid can be isolated from natural sources or synthesized chemically by the oxidation of L-sorbose as in variations of the Reichstein process (U.S. Pat. No. 2,265,121).

It remains desirable to have methods for the production of ascorbic acid by convenient processes. Two main requirements in the production of ascorbic acid are that the synthesis should be enantioselective, because only the L-enantiomer of ascorbic acid is biologically active, and that the environment of the final steps of the process should be non-oxidative, because ascorbic acid is very easily oxidized.

One possible approach is the production of L-ascorbic acid from microorganisms. Microorganisms can be easily grown on an industrial scale. Although the production of L-ascorbic acid from microorganisms and fungi has been reported in the past, recent evidence proves that L-ascorbic acid analogues, and not L-ascorbic acid, are found (Huh W. K. et al. 1998, Mol. Microbiol. 30, 4, 895–903)(Hancock R. D. et al., 2000, FEMS Microbiol. Let. 186, 245–250) (Dumbrava V. A. et al. 1987, BBA 926, 331–338)(Nick J. A. et al., 1986, Plant Science, 46, 181–187). In yeasts (Candida and Saccharomyces species), the production of erythroascorbic acid has been reported (Huh W. K. et al., 1994, Eur. J. Biochem, 225, 1073–1079)(Huh W. K. et al., 1998, Mol. Microbiol. 30, 4, 895–903). In such yeasts, a physiological pathway has been proposed proceeding from D-glucose via D-arabinose and D-arabinono-1,4-lactone to erythroascorbic acid (Kim S. T. et al., 1996, BBA, 1297, 1–8). The enzymes D-arabinose dehydrogenase and D-arabinono-1,4-lactone oxidase from *Candida albicans* as well as *S. cerevisiae* have been characterized. Interestingly, L-galactose and L-galactono-1,4-lactone are substrates for these activities in vitro.

In vivo production of L-ascorbic acid has been obtained by feeding L-galactono-1,4-lactone to wild-type Candida cells (International Patent Application WO85/01745). Recently it has been shown that wild-type *S. cerevisiae* cells accumulated intracellularly L-ascorbic acid when incubated with L-galactose, L-galactono-1,4-lactone, or L-gulono-1,4-lactone (Hancock et al., 2000, FEMS Microbiol. Lett. 186, 245–250)(Spickett C. M. et al., 2000, Free Rad. Biol. Med. 28, 183–192).

Wild-type Candida cells incubated with L-galactono-1,4-lactone accumulate L-ascorbic acid in the medium, suggesting that this yeast has a biological mechanism for the release of the intracellular accumulated L-ascorbic acid; indeed, L-ascorbic acid is a complex molecule and it is scientifically reasonable that its accumulation in the medium is not related to a simple diffusion process, but should depend on facilitated or active transport. This conclusion is supported by the identification and characterization of L-ascorbic acid transporters in higher eukaryotic (mammalian) cells (Daruwala R. et al., 1999, FEBS Letters. 460, 480–484). However, L-ascorbate transporters have not been described among the yeast genera. Nevertheless, while Candida cells growing in media containing L-galactono-1,4-lactone accumulate L-ascorbic acid in the medium, accumulation in the medium of L-ascorbic acid from wild-type *S. cerevisiae* cells has, surprisingly, never been described.

A desirable method for the large-scale production of ascorbic acid comprises the use of genetically engineered microorganisms (i.e., recombinant microorganisms). Both prokaryotic and eukaryotic microorganisms are today easily and successfully used for the production of heterologous proteins as well as for the production of heterologous metabolites. Among prokaryotes, *Escherichia coli* and *Bacillus subtilis* are often used. Among eukaryotes, the yeasts *S. cerevisiae* and *Kluyveromyces lactis* are often used. Despite the great success of these hosts, only one example has been described for the production of L-ascorbic acid by transformed microbial cells. Since only eukaryotic cells are natural L-ascorbic acid producers, it is even more surprising that only a prokaryotic transformed microbial host has been described to lead to the intracellular accumulation of L-ascorbic acid. Lee et al. (Appl. Environment. Microbiol., 1999, 65, 4685–4687), showed that the cloning of the *S. cerevisiae* gene encoding D-arabinono-1,4-lactone oxidase into E. coli allows the production of L-ascorbic acid from *E. coli* incubated with L-galactono- 1,4-lactone. Accumulation of L-ascorbic acid was observed only at the intracellular level.

No experimental data have been described in the literature about the production of L-ascorbic acid from transformed eukaryotic microorganisms. Østergaard et al. cloned the gene encoding L-galactono-1,4-lactone dehydrogenase from cauliflower in the yeast *S. cerevisiae* (J. Biol. Chem., 1997, 272, 48, 30009–30016). While, in vitro, the authors found L-galactono-1,4-lactone dehydrogenase activity in the yeast cell extract (cytochrome c assay, see Østergaard et al.), no production of L-ascorbic acid was proven in vivo.

Berry et al., International Patent Appln. WO 99/64618 discuss the potential use of the plant biosynthetic pathway of ascorbic acid; special emphasis is given to the activity catalyzing the conversion of GDP-D-mannose to GDP-L-galactose. However, characterization of the enzyme catalyzing this step has not been presented in detail. An overexpressed *E. coli* homologue turned out to be inactive.

Smirnoff et al., WO 99/33995, discuss the use of L-galactose dehydrogenase for production of ascorbic acid. The enzyme was purified from pea seedlings and the N-terminal protein sequence was determined. The complete sequence is not known and has not yet been reported. The L-galactose dehydrogenase enzyme partial sequence was 72% identical to amino acids 5–22 of an unidentified putative coding sequence from *Arabidopsis thaliana*, accession no. 3549669.

Roland et al., U.S. Pat. Nos. 4,595,659 and 4,916,068, discuss the use of non-recombinant *Candida* strains to convert L-galactonic substrates to L-ascorbic acid. Roland et al. described the responsible enzyme as L-galactono-1,4-lactone oxidase.

Kumar, WO 00/34502, discusses the production of L-ascorbic acid in *Candida blankii* and *Cryptococcus dimennae* yeast capable of using 2-keto-L-gulonic acid as a sole carbon source in the production. Kumar specifically excludes the production from yeast by a pathway involving L-galactonolactone oxidase or by conversion of L-galactonic precursors.

It remains desirable to have methods for the production of ascorbic acid by a convenient fermentation process.

SUMMARY OF THE INVENTION

In one embodiment, this invention relates to a method of generating ascorbic acid, comprising (i) culturing a Kluyveromyces spp. or a Zygosaccharomyces spp. yeast in a medium comprising an ascorbic acid precursor, thereby forming ascorbic acid, and (ii) isolating the ascorbic acid.

In a second embodiment, the present invention relates to a method of generating ascorbic acid, comprising (i) culturing a recombinant yeast in a medium comprising an ascorbic acid precursor, thereby forming ascorbic acid, and (ii) isolating the ascorbic acid. Preferably, the recombinant yeast accumulates ascorbic acid in the medium at a level greater than the background. Also preferably, the recombinant yeast produces ascorbic acid at a yield greater than about 35% from the precursor.

In a third embodiment, the present invention relates to a method of stabilizing ascorbic acid in a medium, comprising culturing a yeast in the medium.

The present invention provides methods for the production of ascorbic acid by a convenient fermentation process.

DESCRIPTION OF ILLUSTRATIVE EMBODIMENTS

Figure 1:
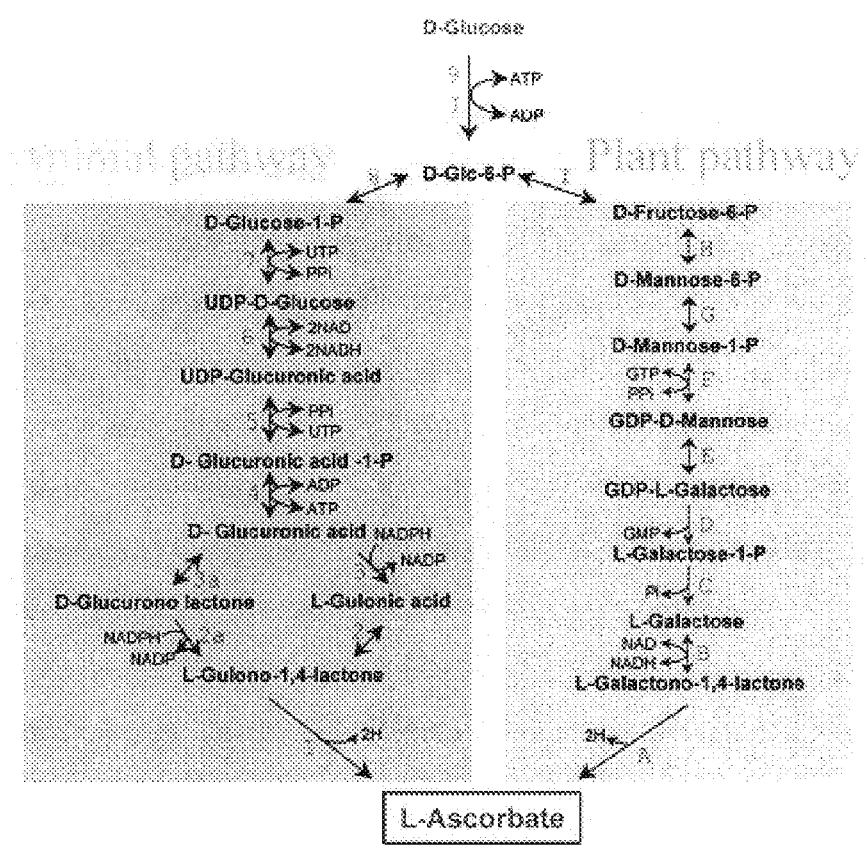
FIG. 1 provides a schematic representation of the current understanding of the physiological biosynthetic pathways leading from D-glucose to L-ascorbic acid in plants or animals, respectively. The following enzymes are involved: A, L-galactono-1,4-lactone dehydrogenase (1.3.2.3), B, L-galactose dehydrogenase, C, sugar phosphatase (3.1.3.23, putative), D, hydrolase (putative), E, GDP-mannose-3,5-epimerase (5.1.3.18), F, mannose-1-phosphate guanylyltransferase (2.7.7.22), G, phosphomannomutase (5.4.2.8), H, mannose-6-phosphate isomerase (5.3.1.8), 1, glucose-6-phosphate isomerase (5.3.1.9), J; hexokinase (2.7.1.1); 1; L-gulono-1,4-lactone oxidase (1.1.3.8); 2; aldonolactonase (3.1.1.17); 2a, glucurono lactone reductase (1.1.1.20) 3; D-glucuronate reductase (1.1.1.19), uronolactonase (3.1.1.19) or spontaneous, 4; D-glucurono kinase (2.7.1.43); 5; glucuronate-1-phosphate uridylyltransferase (2.7.7.44); 6; UDP-D-glucose dehydrogenase (1.1.1.22); 7, UTP-glucose-1-phophate uridylyltransferase (2.7.7.9); 8, phosphoglucomutase (5.4.2.2), 9, hexokinase (2.7.1.1). However, it has to be stressed that in the scope of the present invention to produce L-ascorbic acid, the enzymes useful are not limited to the enzymes of the physiological pathways.

In one embodiment, this invention relates to a method of generating ascorbic acid, comprising (i) culturing a Kluyveromyces spp. or a Zygosaccharomyces spp. yeast in a medium comprising an ascorbic acid precursor, thereby forming ascorbic acid, and (ii) isolating the ascorbic acid. This method is based on the scientific observation that wild-type yeast of the genus Kluyveromyces or Zygosaccharomyces are capable of generating L-ascorbic acid when cultured on a medium containing an ascorbic acid pathway precursor. Preferably, the yeast is Z. bailii or K. lactis. More preferably, the yeast is Z. bailii ATCC 60483 or K lactis PM6-7A.

The medium in which the yeast is cultured can be any medium known in the art to be suitable for this purpose. Culturing techniques and media are well known in the art. Typically, but it is not limited to, culturing is performed by aqueous fermentation in an appropriate vessel. Examples for a typical vessel for yeast fermentation comprise a shake flask or a bioreactor.

The medium comprises any component required for the growth of the yeast and one or more precursors for the production of ascorbic acid. Components for growth of the yeast and precursors for the production of ascorbic acid may or may be not identical.

The medium comprises a carbon source, such as glucose or other carbohydrates (such as sucrose, fructose, lactose, D-galactose, or hydrolysates of vegetable matter, among others). Typically, the medium also comprises a nitrogen source, either organic or inorganic, and optionally the medium may also comprise components such as amino acids; purines; pyrimidines; corn steep liquor; yeast extract; protein hydrolysates; water-soluble vitamins, such as B complex vitamins; or inorganic salts such as chlorides, hydrochlorides, phosphates, or sulfates of Ca, Mg, Na, K, Fe, Ni, Co, Cu, Mn, Mo, or Zn, among others. Further components known to one of ordinary skill in the art to be useful in yeast culturing or fermentation can also be included. The medium may or may be not buffered.

The medium also comprises an ascorbic acid precursor. The ascorbic acid precursor is any compound that, in the yeast, can be converted, either directly or through intermediate steps, into L-ascorbic acid. Ascorbic acid precursors include, but are not limited to D-glucose; trehalose; fructose; D-glucose-6-P; D-glucose-1-P; UDP-D-glucose; UDP-glucuronic acid; D-glucuronic acid-1-P; D-glucuronic acid; D-glucurono lactone; L-gulonic acid; D-fructose-6-P; D-mannose-6-P; D-mannose-1-P; GDP-D-mannose; GDP-L-galactose; L-galactose-1-P; L-galactose; L-gulono-1,4-lactone; or L-galactono-1,4-lactone. Preferably, the ascorbic acid precursor is selected from D-glucose; L-galactose; L-galactono-1,4-lactone; or L-gulono-1,4-lactone. Two or more ascorbic acid precursors can also be used.

During the course of the fermentation, the ascorbic acid precursor is internalized by the yeast and converted, through one or more steps, into L-ascorbic acid. The L-ascorbic acid so produced can be contained within the yeast, or can be accumulated in the medium at greater than background levels.

A preferred medium comprises glucose, YNB, and at least one of L-galactono-1,4-lactone; L-gulono-1,4-lactone; or L-galactose.

After culturing has progressed for a sufficient length of time to produce a desired concentration of L-ascorbic acid in the yeast, the culture medium, or both, the L-ascorbic acid is isolated. "Isolated," as used herein to refer to ascorbic acid, means being brought to a state of greater purity by separation of ascorbic acid from at least one non-ascorbic acid component of the yeast or the medium. Preferably, the isolated ascorbic acid is at least about 95% pure, more preferably at least about 99% pure.

To isolate L-ascorbic acid from the yeast, the first step of isolation, after the yeast is separated from the medium, typically is lysing of the yeast by chemical or enzymatic treatment, treatment with glass beads, sonication, freeze/thaw cycling, or other known techniques. L-ascorbic acid can be purified from the membrane, protein, and nucleic acid fractions of the yeast lysate by appropriate techniques, such as centrifugation, filtration, microfiltration, ultrafiltration, nanofiltration, liquid-liquid extraction, crystallization, enzymatic treatment with nuclease or protease, or chromatography, among others.

To isolate L-ascorbic acid accumulated in the medium, the isolation comprises purifying the ascorbic acid from the medium. Purification can be performed by known techniques, such as the use of an ion exchange resin, activated carbon, microfiltration, ultrafiltration, nanofiltration, liquid-liquid extraction, crystallization, or chromatography, among others.

L-ascorbic acid can be isolated from both the yeast and the medium.

If the yeast accumulates L-ascorbic acid in the medium during the culturing step, preferably the concentration of L-ascorbic acid is stabilized or allowed to increase.

In a second embodiment, the present invention relates to a method of generating ascorbic acid, comprising (i) culturing a recombinant yeast in a medium comprising an ascorbic acid precursor, thereby forming ascorbic acid, and (ii) isolating the ascorbic acid.

A "recombinant" yeast is a yeast that contains a nucleic acid sequence not naturally occurring in the yeast or an additional copy or copies of an endogenous nucleic acid sequence, wherein the nucleic acid sequence is introduced into the yeast or an ancestor cell thereof by human action. Recombinant DNA techniques are well-known, such as in Sambrook et al., *Molecular Genetics: A Laboratory Manual*, Cold Spring Harbor Laboratory Press, which provides further information regarding various techniques known in the art and discussed herein. In this embodiment, a coding region of the homologous and/or heterologous gene is isolated from an organism, which possesses the gene. The organism can be a bacterium, a prokaryote, a eukaryote, a microorganism, a fungus, a plant, or an animal.

Genetic material comprising the coding region can be extracted from cells of the organism by any known technique. Thereafter, the coding region can be isolated by any appropriate technique. In one known technique, the coding region is isolated by, first, preparing a genomic DNA library or a cDNA library, and second, identifying the coding region in the genomic DNA library or cDNA library, such as by probing the library with a labeled nucleotide probe selected to be or presumed to be at least partially homologous with the coding region, determining whether expression of the coding region imparts a detectable phenotype to a library microorganism comprising the coding region, or amplifying the desired sequence by PCR. Other known techniques for isolating the coding region can also be used.

The recombinant yeast can be selected from any known genus and species of yeast. Yeasts are described by N. J. W. Kreger-van Rij, "The Yeasts," Vol. 1 of Biology of Yeasts, Ch. 2, A. H. Rose and J. S. Harrison, Eds. Academic Press, London, 1987. For example, the yeast genus can be Saccharomyces, Zygosaccharomyces, Candida, Hansenula, Kluyveromyces, Debaromyces, Nadsonia, Lipomyces, Torulopsis, Kloeckera, Pichia, Schizosaccharomyces, Trigonopsis, Brettanomyces, Cryptococcus, Trichosporon, Aureobasidium, Phaffia, Rhodotorula, Yarrowia, or Schwanniomyces, among others. Saccharomyces, Zygosaccharomyces, Kluyveromyces spp. are preferred. More preferably, the yeasts are *S. cerevisiae*, *Z. bailii* and *K lactis*. Even more preferably, the yeast is *S. cerevisiae* strain GRF18U or W3031B, *Z. bailii* ATCC 60483, or *K. lactis* PM6-7A.

Preferably, a recombinant yeast of the present invention is not able to produce L-ascorbic acid from 2-keto-L-gulonic acid.

Preferably, the recombinant yeast comprises at least one coding region encoding an enzyme associated with the conversion of a carbon source to ascorbate.

In a preferred embodiment of the present invention, the coding region introduced into the recombinant yeast encodes an enzyme selected from L-galactose dehydrogenase (LGDH), L-galactono-1,4-lactone dehydrogenase (AGD), D-arabinose dehydrogenase (ARA), D-arabinono-1,4-lactone oxidase (ALO), L-gulono-1,4-lactone oxidase (RGLO).

In one more preferred embodiment, the coding region of L-galactose dehydrogenase (LGDH), L-galactono-1,4-lactone dehydrogenase (AGD), D-arabinose dehydrogenase (ARA), D-arabinono-1,4-lactone oxidase (ALO), L-gulono-1,4-lactone oxidase (RGLO) are isolated from *A. thaliana* or *S. cerevisiae* or *Rattus norvegicus*. It should be noted that the term "isolated," as used herein in reference to a nucleic acid sequence, refers to the ultimate source, not the immediate source, of the coding region. That is, a coding region is "isolated" from an organism if it encodes a protein sequence substantially identical to that of the same protein purified from cells of the organism. In even more preferred embodiments, the coding regions encoding LGDH and AGD are isolated from A. thaliana, the coding regions encoding ALO and ARA are isolated from *S. cerevisiae*, and the coding region encoding RGLO is isolated from *R. norvegicus*.

In another more preferred embodiment, the amino acid sequence of the LGDH enzyme has at least about 70%, more preferably about 80%, and most preferably about 90% similarity with SEQ ID NO:11; the amino acid sequence of the AGD enzyme has at least about 70%, more preferably about 80%, and most preferably about 90% similarity with SEQ ID NO:1 or SEQ ID NO:3; the amino acid sequence of the ARA enzyme has at least about 70%, more preferably about 80%, and most preferably about 90% similarity with SEQ ID NO:20; the amino acid sequence of the ALO enzyme has at least about 70%, more preferably about 80%, and most preferably about 90% similarity with SEQ ID NO:5 or SEQ ID NO:7; the amino acid sequence of the RGLO enzyme has at least about 70%, more preferably about 80%, and most preferably about 90% similarity with SEQ ID NO:9; wherein "similarity" is determined by a sequence alignment performed using the CLUSTAL program.

In another more preferred embodiment, the amino acid sequence of the LGDH enzyme has at least about 70%, more preferably about 80%, and most preferably about 90% identity with SEQ ID NO:11; the amino acid sequence of the AGD enzyme has at least about 70%, more preferably about 80%, and most preferably about 90% identity with SEQ ID NO:1 or SEQ ID NO:3; the amino acid sequence of the ARA enzyme has at least about 70%, more preferably about 80%, and most preferably about 90% identity with SEQ ID NO:20; the amino acid sequence of the ALO enzyme has at least about 70%, more preferably about 80%, and most preferably about 90% identity with SEQ ID NO:5 or SEQ ID NO:7; the amino acid sequence of the RGLO enzyme has at least about 70%, more preferably about 80%, and most preferably about 90% identity with SEQ ID NO:9; wherein "identity" is determined by a sequence alignment performed using the CLUSTAL program.

In another more preferred embodiment, the coding region encoding the LGDH enzyme has at least about 70%, more preferably about 80%, and most preferably about 90% identity with SEQ ID NO 12; the coding region encoding the AGD enzyme has at least about 70%, more preferably about 80%, and most preferably about 90% identity with SEQ ID NO 2 or SEQ ID NO 4; the coding region encoding the ARA enzyme has at least about 70%, more preferably about 80%, and most preferably about 90% identity with SEQ ID NO 21; the coding region encoding the ALO enzyme has at least about 70%, more preferably about 80%, and most preferably about 90% identity with SEQ ID NO 6 or SEQ ID NO 8; the coding region encoding the RGLO enzyme has at least about 70%, more preferably about 80%, and most preferably about 90% identity with SEQ ID NO 10; wherein "identity" is determined by a sequence alignment performed using the CLUSTAL program.

In another preferred embodiment, wherein the enzyme is ARA, the enzyme comprises motif I and motif II of the aldo-keto reductase (AKR) superfamily, specifically the amino acid sequences GXRXXDXAXXXXXEXXXG (SEQ ID NO:13) and GXXN (SEQ ID NO:26), respectively (Kim S. T. et al. 1998, BBA, 1429, 29–39).

In a more preferred embodiment, the recombinant yeast further comprises at least one coding region encoding an enzyme associated with the conversion of a carbon source to L-galactose.

Preferably, a coding region encoding a desired enzyme is incorporated into the yeast in such a manner that the desired enzyme is produced in the yeast and is substantially functional. Such a yeast may be referred to herein as being "functionally transformed."

Once the coding region has been isolated, it can be prepared for transformation into and expression in the yeast useful in the present invention. At minimum, this involves the insertion of the coding region into a vector and operable linkage to a promoter found on the vector and active in the target organism (i.e., in the present invention, a yeast). Any vector (integrative, chromosomal or episomal) can be used.

Any promoter active in the target host (homologous or heterologous, constitutive, inducible or repressible) can be used. Such insertion often involves the use of restriction endonucleases to "open up" the vector at a desired point where operable linkage to the promoter is possible, followed by ligation of the coding region into the desired point. If desired, before insertion into the vector, the coding region can be prepared for use in the target organism. This can involve altering the codons used in the coding region to more fully match the codon use of the target organism; changing sequences in the coding region that could impair the transcription or translation of the coding region or the stability of an mRNA transcript of the coding region; or adding or removing portions encoding signaling peptides (regions of the protein encoded by the coding region that direct the protein to specific locations (e.g. an organelle, the membrane of the cell or an organelle, or extracellular secretion)), among other possible preparations known in the art. In one embodiment of the present invention, the L-galactono-1,4-lactone dehydrogenase protein (AGD) comprises a signaling peptide and the coding region encoding the L-galactono-1,4-lactone dehydrogenase also encodes the signaling peptide. In another embodiment of the present invention, the L-galactono-1,4-lactone dehydrogenase protein (AGD) does not comprise a signaling peptide and the coding region encoding the L-galactono-1,4-lactone dehydrogenase also does not encode the signaling peptide. Specifically, the AGD sequence given in SEQ ID NO:1 comprises a signaling peptide of amino acids 1–100, and the AGD sequence given in SEQ ID NO:2 comprises a signaling peptide of amino acids 1–90. As one of skill in the art will recognize, deletion of a nucleic acid sequence encoding a signaling peptide from a longer nucleic acid sequence encoding a desired enzyme may require the addition of an in-frame ATG codon to allow for proper initiation of translation of the desired enzyme.

Regardless whether the coding region is modified, when the coding region is inserted into the vector, it is operably linked to a promoter active in the yeast. A promoter, as is known, is a DNA sequence that can direct the transcription of a nearby coding region. As already described, the promoter can be constitutive, inducible or repressible. Inducible promoters can be induced by the addition to the medium of an appropriate inducer molecule, which will be determined by the identity of the promoter. Repressible promoters can be repressed by the addition to the medium of an appropriate repressor molecule, which will be determined by the identity of the promoter. Constitutive promoters are preferred, as the use of an inducer or repressor molecule is not required. A preferred constitutive promoter is the *S. cerevisiae* triose-phosphateisomerase (TPI) promoter.

The vector comprising the coding region operably linked to the promoter can be a plasmid, a cosmid, or a yeast artificial chromosome, among others known in the art to be appropriate for use in yeast genera. In addition to the coding region operably linked to the promoter, the vector can also comprise other genetic elements. For example, if the vector is not expected to integrate into the yeast genome, the vector desirably comprises an origin of replication, which allows the vector to be passed on to progeny cells of a yeast comprising the vector. If integration of the vector into the yeast genome is desired, the vector can comprise sequences homologous to sequences found in the yeast genome, and can also comprise coding regions that can facilitate integration. To determine which yeast cells are transformed, the vector preferably comprises a selectable marker or screenable marker which imparts a phenotype to the yeast that distinguishes it from untransformed yeast, e.g. it survives on a medium comprising an antibiotic fatal to untransformed yeast or it metabolizes a component of the medium into a product that the untransformed yeast does not, among other phenotypes. In addition, the vector may comprise other genetic elements, such as restriction endonuclease sites and others typically found in vectors.

After the vector is prepared, with the coding region operably linked to the promoter, the yeast is transformed with the vector (i.e. the vector is introduced into at least one of the cells of a yeast population). Techniques for yeast transformation are well established, and include electroporation, microprojectile bombardment, and the LiAc/ssDNA/PEG method, among others. Yeast cells, which are transformed, can then be detected by the use of a screenable or selectable marker on the vector. It should be noted that the phrase "transformed yeast" has essentially the same meaning as "recombinant yeast," as defined above. The transformed yeast can be one that received the vector in a transformation technique, or can be a progeny of such a yeast.

After a recombinant yeast has been obtained, the yeast is cultured in a medium. The medium is as described above.

A preferred medium comprises glucose, YNB, and L-galactono-1,4-lactone. Preferred recombinant yeasts which can be cultured in this medium include S. cerevisiae strain GRF18U yeast bearing a S. cerevisiae TPI promoter operably linked to a coding region encoding A. thaliana L-galactono-1,4-lactone dehydrogenase (AGD); and S. cerevisiae strain GRF18U yeast bearing a S. cerevisiae TPI promoter operably linked to a coding region encoding S. cerevisiae D-arabinono-1,4-lactone oxidase (ALO).

Another preferred medium comprises glucose, YNB and L-gulono-1,4-lactone. One particularly preferred recombinant yeast which can be cultured in this medium include S. cerevisiae strain GRF18U bearing a S. cerevisiae TPI promoter operably linked to a coding region encoding R. norvegicus L-gulono-1,4-lactone oxidase (RGLO).

Another preferred medium comprises glucose, YNB and L-galactose. One particularly preferred transformed yeast which can be cultured in this medium is S. cerevisiae strain GRF18U yeast bearing (i) a S. cerevisiae TPI promoter operably linked to a coding region encoding A. thaliana L-galactono-1,4-lactone dehydrogenase (AGD) and (ii) a TPI promoter operably linked to a coding region encoding A. thaliana L-galactose dehydrogenase (LGDH). A second particularly preferred transformed yeast which can be cultured in this medium is S. cerevisiae strain GRF18U yeast comprising (i) a TPI promoter operably linked to a coding region encoding S. cerevisiae D-arabinono-1,4-lactone oxidase (ALO) and (ii) a TPI promoter operably linked to a coding region encoding A. thaliana L-galactose dehydrogenase (LGDH). A third particularly preferred transformed yeast which can be cultured in this medium is S. cerevisiae strain GRF18U yeast comprising (i) a TPI promoter operably linked to a coding region encoding S. cerevisiae D-arabinono-1,4-lactone oxidase (ALO) and (ii) a TPI promoter operably linked to a coding region encoding S. cerevisiae D-arabinose dehydrogenase (ARA).

As described for non-recombinant yeast, above, during the course of the fermentation, the ascorbic acid precursor is converted, through one or more steps, into L-ascorbic acid.

While the non-recombinant yeast cells (described above) incubated in similar media typically do not accumulate ascorbic acid above background levels in the medium, surprisingly, the particularly preferred recombinant strains herein described are able to accumulate considerable amounts of L-ascorbic acid above background levels. The only exception relates to a yeast transformed with only LGDH, which does not accumulate L-ascorbic acid above background levels, that indicates the LGDH expression is not the limiting factor. The data taken together indicate that the conversion of L-galactono-1,4-lactone to ascorbic acid is the limiting factor in the pathway leading from L-galactose to ascorbic acid.

Therefore, in a preferred embodiment, the recombinant yeast accumulates L-ascorbic acid in the medium above background levels.

Isolation of the ascorbic acid from the media is as described above. Yields of ascorbic acid of greater than about 35% have been observed, as will be described in the Examples below. Therefore, in a further preferred embodiment, the recombinant yeast produce ascorbic acid with a yield higher than 35% of the precursor. The term "yield" refers to the amount of ascorbic acid (molar as well as weight/volume) produced divided by the amount of precursor consumed (molar as well as weight/volume) multiplied by 100.

The following definitions are provided in order to aid those skilled in the art in understanding the detailed description of the present invention.

The term "accumulation of ascorbic acid above background levels" refers to the accumulation of ascorbic acid above the undetectable levels as determined using the procedures described herein.

"Ascorbic acid" as well as "ascorbate" as used herein, refers to L-ascorbic acid.

"Ascorbic acid precursor" is a compound that can be converted by a yeast of the present invention, either directly or through one or more intermediates, into L-ascorbic acid.

"Amplification" refers to increasing the number of copies of a desired nucleic acid molecule or to increase the activity of an enzyme, by whatsoever means.

"Codon" refers to a sequence of three nucleotides that specify a particular amino acid.

"DNA ligase" refers to an enzyme that covalently joins two pieces of double-stranded DNA.

"Electroporation" refers to a method of introducing foreign DNA into cells that uses a brief, high voltage DC charge to permeabilize the host cells, causing them to take up extra-chromosomal DNA.

"Endonuclease" refers to an enzyme that hydrolyzes double stranded DNA at internal locations.

Enzyme 1.1.3.37, D-arabinono-1,4-lactone oxidase, refers to a protein that catalyzes the conversion of D-arabinono-1,4-lactone+$O_2$ to D-erythroascorbate+$H_2O_2$. The same enzyme due to broadness of substrate range catalyses the conversion of L-galactono-1,4-lactone+$O_2$ to L-ascorbic acid+$H_2O_2$. Erroneously the same enzyme is referred to as L-galactono-1,4-lactone oxidase (enzyme 1.1.3.24) (see Huh, W. K. et al, 1998, Mol. Microbiol. 30, 4, 895–903)

Enzyme 1.3.2.3, L-galactono-1,4-lactone dehydrogenase, refers to a protein that catalyzes the conversion of L-galactono-1,4-lactone+2 ferricytochrome C to L-ascorbic acid+2 ferrocytochrome C.

Enzyme 1.1.3.8, L-gulono-1,4-lactone oxidase, refers to a protein that catalyzes the oxidation of L-gulono-1,4-lactone to L-xylo-hexulonolactone which spontaneously isomerizes to L-ascorbic acid.

Other enzymes of interest, and their classification numbers, are as follows:

| | |
|---|---|
| Hexokinase | 2.7.1.1 |
| Glucose-6-P isomerase | 5.3.1.9 |
| Mannose-6-P isomerase | 5.3.1.8 |
| phosphomannomutase | 5.4.2.8 |
| Mannose-1-P guanylyltransferase | 2.7.7.22 |
| GDP-Mannose 3,5-epimerase | 5.1.3.18 |
| Sugar phosphatase | 3.1.3.23 |
| L-Galactose-dehydrogenase | *) |
| L-Galactono-1,4-lactone dehydrogenase | 1.3.2.3 |
| D-Mannose kinase | 2.7.1.1 |
| Phosphoglucomutase | 5.4.2.2 |
| UTP-Glucose-1-P uridylyl transferase | 2.7.7.9 |
| UDP-D-Glucose dehydrogenase | 1.1.1.22 |
| UDP-Glucuronate 4-epimerase | 5.1.3.6 |
| glucuronate-1-P uridylyltransferase | 2.7.7.44 |
| D-Glucuronokinase | 2.7.1.43 |
| D-Glucuronate reductase | 1.1.1.19 |
| Aldonolactonase | 3.1.1.17 |
| L-Gulono-1,4-lactone oxidase | 1.1.3.8 |
| Uronolactonase | 3.1.1.19 |
| Glucuronolactone reductase activity | 1.1.1.20 |
| L-Galactono-1,4-lactone 3-epimerase | *) |
| Galacturonate-1-P uridylyltransferase | *) |
| Galacturonokinase | 2.7.1.44 |
| Hexuronate (D-galacturonate) reductase | *) |

| | |
|---|---|
| -continued | |
| Myoinositol 1-P synthase | 5.5.1.4 |
| Myoinositol 1-P monophosphatase | 3.1.3.25 |
| Myoinositol oxygenase | 1.13.99.1 |
| D-Galactokinase | 2.7.1.6 |
| UTP-Hexose 1-P uridylyltransferase | 2.7.7.10 |
| UDP-Glucose 4-epimerase | 5.1.3.2 |
| Suc synthase | 2.4.1.13 |
| Fructokinase | 2.7.1.4 |

\*) Classification number not available in databases.

The term "expression" refers to the transcription of a gene to produce the corresponding mRNA and translation of this mRNA to produce the corresponding gene product, i.e., a peptide, polypeptide, or protein.

The phrase "functionally linked" or "operably linked" refers to a promoter or promoter region and a coding or structural sequence in such an orientation and distance that transcription of the coding or structural sequence may be directed by the promoter or promoter region.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The term "genome" encompasses both the chromosomes and plasmids within a host cell. Encoding DNAs of the present invention introduced into host cells can therefore be either chromosomally integrated or plasmid-localized.

"Heterologous DNA" refers to DNA from a source different than that of the recipient cell.

"Homologous DNA" refers to DNA from the same source as that of the recipient cell.

"Hybridization" refers to the ability of a strand of nucleic acid to join with a complementary strand via base pairing. Hybridization occurs when complementary sequences in the two nucleic acid strands bind to one another.

The term "medium" refers to the chemical environment of the yeast comprising any component required for the growth of the yeast or the recombinant yeast and one or more precursors for the production of ascorbic acid. Components for growth of the yeast and precursors for the production of ascorbic acid may or may be not identical.

"Open reading frame (ORF)" refers to a region of DNA or RNA encoding a peptide, polypeptide, or protein.

"Plasmid" refers to a circular, extra chromosomal, replicatable piece of DNA.

"Polymerase chain reaction (PCR)" refers to an enzymatic technique to create multiple copies of one sequence of nucleic acid. Copies of DNA sequence are prepared by shuttling a DNA polymerase between two amplimers. The basis of this amplification method is multiple cycles of temperature changes to denature, then re-anneal amplimers, followed by extension to synthesize new DNA strands in the region located between the flanking amplimers.

The term "promoter" or "promoter region" refers to a DNA sequence, usually found upstream (5') to a coding sequence, that controls expression of the coding sequence by controlling production of messenger RNA (mRNA) by providing the recognition site for RNA polymerase and/or other factors necessary for start of transcription at the correct site.

A "recombinant cell" or "transformed cell" is a cell that contains a nucleic acid sequence not naturally occurring in the cell or an additional copy or copies of an endogenous nucleic acid sequence, wherein the nucleic acid sequence is introduced into the cell or an ancestor thereof by human action.

The term "recombinant vector" or "recombinant DNA or RNA construct" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a nucleic acid molecule in which one or more sequences have been linked in a functionally operative manner. Such recombinant constructs or vectors are capable of introducing a 5' regulatory sequence or promoter region and a DNA sequence for a selected gene product into a cell in such a manner that the DNA sequence is transcribed into a functional mRNA, which may or may not be translated and therefore expressed.

"Restriction enzyme" refers to an enzyme that recognizes a specific sequence of nucleotides in double stranded DNA and cleaves both strands; also called a restriction endonuclease. Cleavage typically occurs within the restriction site or close to it.

"Selectable marker" refers to a nucleic acid sequence whose expression confers a phenotype facilitating identification of cells containing the nucleic acid sequence. Selectable markers include those, which confer resistance to toxic chemicals (e.g. ampicillin, kanamycin) or complement a nutritional deficiency (e.g. uracil, histidine, leucine).

"Screenable marker" refers to a nucleic acid sequence whose expression imparts a visually distinguishing characteristic (e.g. color changes, fluorescence).

"Transcription" refers to the process of producing an RNA copy from a DNA template.

"Transformation" refers to a process of introducing an exogenous nucleic acid sequence (e.g., a vector, plasmid, or recombinant nucleic acid molecule) into a cell in which that exogenous nucleic acid is incorporated into a chromosome or is capable of autonomous replication. A cell that has undergone transformation, or a descendant of such a cell, is "transformed" or "recombinant." If the exogenous nucleic acid comprises a coding region encoding a desired protein, and the desired protein is produced in the transformed yeast and is substantially functional, such a transformed yeast is "functionally transformed."

"Translation" refers to the production of protein from messenger RNA.

The term "yield" refers to the amount of ascorbic acid produced (molar or weight/volume) divided by the amount of precursor consumed (molar or weight/volume) multiplied by 100.

"Unit" of enzyme refers to the enzymatic activity and indicates the amount of micromoles of substrate converted per mg of total cell proteins per minute.

"Vector" refers to a DNA or RNA molecule (such as a plasmid, cosmid, bacteriophage, yeast artificial chromosome, or virus, among others) that carries nucleic acid sequences into a host cell. The vector or a portion of it can be inserted into the genome of the host cell.

LIST OF ABBREVIATIONS

Asc L-ascorbic acid (vitamin C)
AGD L-galactono-1,4-lactone dehydrogenase (without signaling peptide, from *A. thaliana*)

ALO D-arabinono-1,4-lactone oxidase from *S. cerevisiae*
ARA D-arabinose dehydrogenase from *S. cerevisiae*
Gal L-galactono-1,4-lactone
Gul L-gulono-1,4-lactone
LGDH L-galactose dehydrogenase from *A. thaliana*
RGLO L-gulono-1,4-lactone oxidase from *R. norvegicus*
TCA trichloro acetic acid
TPI triosephosphateisomerase

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

MATERIALS AND METHODS

1. Determination of Ascorbic Acid

Ascorbic acid was determined spectrophotometrically following a method after Sullivan et al. (1955, Assoc. Off. Agr. Chem., 38, 2, 514–518). 135 $\mu$l of sample were mixed in a cuvette with 40 $\mu$l of $H_3PO_4$ (85%). Then 675 $\mu$l $\alpha,\alpha'$-Bipyridyl (0.5%) and 135 $\mu$l $FeCl_3$ (1%) were added. After 10 min the absorbance at 525 nm was measured. The identity of the ascorbic acid was confirmed by HPLC (Tracer Extrasil Column C8, 5 $\mu$M, 15×0.46 cm, Teknokroma, S. Coop. C. Ltda. # TR-016077; Eluent: 5 mM cetyltrimethylammonium bromide, 50 mM $KH_2PO_4$ in 95/5 $H_2O$/Acetonitrile; Flow rate: 1 ml min$^{-1}$, Detection UV @254 nm) with pure L-ascorbic acid (Aldrich, A9,290-2) as standard.

2. Determination of Protein Concentration

Protein concentrations were determined following Lowry's method (Lowry O. H. et al., 1951, J. Biol. Chem. 193, 265–275), using the Bio-Rad DC Protein Assay Kit II (Cat. Nr. 500-0112) with BSA as standard.

3. Amplification of Specific Gene Sequences

To amplify specific gene sequences, PfuTurbo DNA polymerase (Stratagene #600252) was used on a GeneAmp PCR System 9700 (PE Appl. Biosystems, Inc.). Standard conditions used were: 400 $\mu$M dNTP, 0.5 $\mu$M primers, 0.5 mM $MgCl_2$ (in addition to the buffer), and 3.75 U Pfu per 100 $\mu$l reaction.

The sequences of the genes used have been publicly reported via Genbank, as follows:

| Gene | Genbank accession no(s). | SEQ ID NO: |
| --- | --- | --- |
| AGD | AL049658 (Gene no. T17F15.200) | 2 |
| AGD homolog from Brassica | Z97060 | 4 |
| ALO | U40390, AB009401 | 6, 8 |
| RGLO | J03536 | 10 |
| ARA | Y13134, Z36018 (ORF YBR149w) | 21 |

The following program was used for amplification of AGD:

| | | |
| --- | --- | --- |
| 94° C. | 5 min | |
| 94° C. | 45 s | |
| 53.5° C. | 30 s | |
| 72° C. | 1 min 40 s | } 33 cycles |
| 72° C. | 7 min | |
| 4° C. | ∞ | |

The following program was used for amplification of ALO:

| | | |
| --- | --- | --- |
| 94° C. | 5 min | |
| 94° C. | 45 s | |
| 50° C. | 30 s | |
| 72° C. | 1 min 40 s | } 33 cycles |
| 72° C. | 7 min | |
| 4° C. | ∞ | |

The following program was used for amplification of ARA:

| | | |
| --- | --- | --- |
| 94° C. | 5 min | |
| 94° C. | 45 s | |
| 56° C. | 30 s | |
| 72° C. | 1 min 40 s | } 33 cycles |
| 72° C. | 7 min | |
| 4° C. | ∞ | |

The following program was used for amplification of LGDH:

| | | |
| --- | --- | --- |
| 94° C. | 5 min | |
| 94° C. | 45 s | |
| 56° C. | 30 s | |
| 72° C. | 1 min 40 s | } 33 cycles |
| 72° C. | 7 min | |
| 4° C. | ∞ | |

The following program was used for amplification of RGLO:

| | | |
| --- | --- | --- |
| 94° C. | 30 s | |
| 94° C. | 5 s | |
| 72° C. | 4 min | 33 cycles |
| 72° C. | 5 min | |
| 4° C. | ∞ | |

Template DNA for AGD and LGDH: 50 ng plasmid cDNA library pFL61 Arabidopsis (ATCC #77500 (Minet M. et al, 1992, Plant J., 2, 417–422)). Template DNA for RGLO: 0.5 ng rat liver marathon-ready cDNA library (Clontech #7471-1). Template DNA for ALO and ARA: 50 ng genomic DNA from *S. cerevisiae* GRF18U, extracted using a standard method. PCR products were blunt end cloned into the EcoRV site of pSTBlue-1 using the perfectly blunt cloning kit from Novagen Inc. (#70191-4).

| Oligonucleotides used | | Gene amplified |
|---|---|---|
| SEQ ID NO: 14: | caagaaggcctaaatgttccgttacgctcc | |
| SEQ ID NO: 15: | atgggcccttaagcagtggtggagactggg | AGD (plant) |
| SEQ ID NO: 16: | tgaggggtcagggtggtttgtttcca | |
| SEQ ID NO: 17: | tggaatcatggtccatgggtacaaaggg | RGLO (rat) |
| SEQ ID NO: 18: | tttcaccatatgtctactatcc | |
| SEQ ID NO: 19: | aaggatcctagtcggacaactc | ALO (yeast) |
| SEQ ID NO: 22: | atgacgaaaatagagcttcgagc | |
| SEQ ID NO: 23: | ttagttctgatggattccacttgg | LGDH (plant) |
| SEQ ID NO: 24: | atgtcttcttcagtagcctcaacc | |
| SEQ ID NO: 25: | ttaatactttaaattgtccaagtttggtc | ARA (yeast) |

4. Plasmid Construction

The naming convention used herein is that pSTBlue-1 containing, for example, AGD in sense direction regarding its multiple cloning site (MCS) was designated pSTB AGD-1. In a further example, pSTBlue-1 containing AGD in antisense direction regarding its MCS was designated pSTB AGD-2, and so on.

Inserts were cloned using the pYX series (R&D Systems, Inc.) below. Standard procedures were employed for all cloning purposes (Sambrook J. et al., *Molecular Genetics: A Laboratory Manual*, Cold Spring Harbor Laboratory Press).

| pSTB AGD-1 | EcoRI | | pYX042 | | | pL AGD |
|---|---|---|---|---|---|---|
| pSTB LGDH-1 | EcoRI | | pYX022 | | | pH LGDH |
| pSTB ALO-1 | EcoRI | | pYX042 | | | pL ALO |
| pSTB ARA-2 | SacI blunt | BamHI | pYX022 | EcoRI blunt | BamHI | pH ARA |
| pSTB RGLO-1 | NotI blunt | KpnI blunt | pYX042 | EcoRI blunt | | pL RGLO |

5. Yeast Cultivation and Examination:

Yeast strains used were *S. cerevisiae* GRF18U (Brambilla, L. et al., 1999, FEMS Microb. Lett. 171, 133–140), W3031B, *Z. bailii* ATCC 60483, and *K. lactis* PM6-7A (Wésolowski-Louvel, M. et al., 1992, Yeast 8, 711–719). All strains were cultivated in shake flasks in minimal medium (0.67% w/v YNB (Difco Laboratories, Detroit, Mich. #919-15), 2% w/v glucose, addition of the appropriate amino acids or adenine or uracil, respectively, to 50 $\mu$g $l^{-1}$) under standard conditions (shaking at 30° C.) The initial optical density at 660 nm was about 0.05.

For incubation with L-galactose the cells were grown over night, then 250 mg $l^{-1}$ of L-galactose were added and the cells were incubated for 24 hr. For incubation with substrates other than L-galactose, the cells were grown in presence of 50 mM or 100 mM of the respective substrates for 72 hr.

Cells were recovered by centrifugation at 4000 rpm for 5 min at 4° C., washed once with cold distilled $H_2O$, and treated as follows: for determination of intracellular ascorbic acid, cells were resuspended in about 3 times the pellet volume of cold 10% TCA, vortexed vigorously, kept on ice for about 20 min then the supernatant was cleared from the cell debris by centrifugation.

6. Yeast Transformation:

Transformation of yeast cells was done following the standard LiAc/ss-DNA/PEG method (Gietz, R. D. and Schiestl, R. H., 1996, Transforming Yeast with DNA, Methods in Mol. and Cell. Biol.). Transformed yeast are being deposited with ATCC, catalog numbers not yet assigned.

EXPERIMENTAL RESULTS

1. Stability of L-ascorbic Acid

Figure 2:
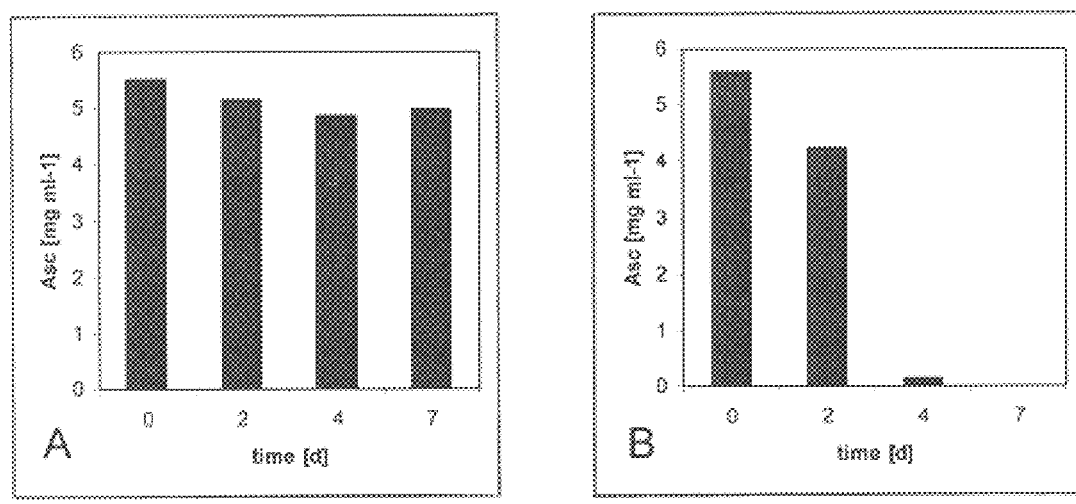
FIGS. 2A–B shows the stability of ascorbic acid under culture conditions. Ascorbic acid was added to mineral medium (2% glucose, 0.67% YNB) and incubated under standard culture conditions for 7 days. The flask of panel A was inoculated at time 0 with non-transformed *S. cerevisiae* GRF18U to an initial $OD^{660}$ of 0.05, whereas the flask of panel B was kept sterile. Samples were taken at the indicated times and the ascorbic acid concentration was determined. Although the ascorbic acid was stable in this medium when growing yeast was present, it was completely degraded within 7 days in sterile medium.

To determine the stability of ascorbic acid under culture conditions, we added ascorbic acid to our standard medium (2% glucose, 0.67% YNB) and incubated the solution in shake flasks shaking at 30° C. FIG. 2 shows the respective results. In sterile medium, ascorbic acid is rapidly degraded (see panel B), whereas it is completely stable if growing yeast is present (see panel A). This result shows that culturing yeast in a medium is a method of stabilizing ascorbic acid.

2. Ascorbic Acid Production From Non-transformed Yeasts

Figure 3:
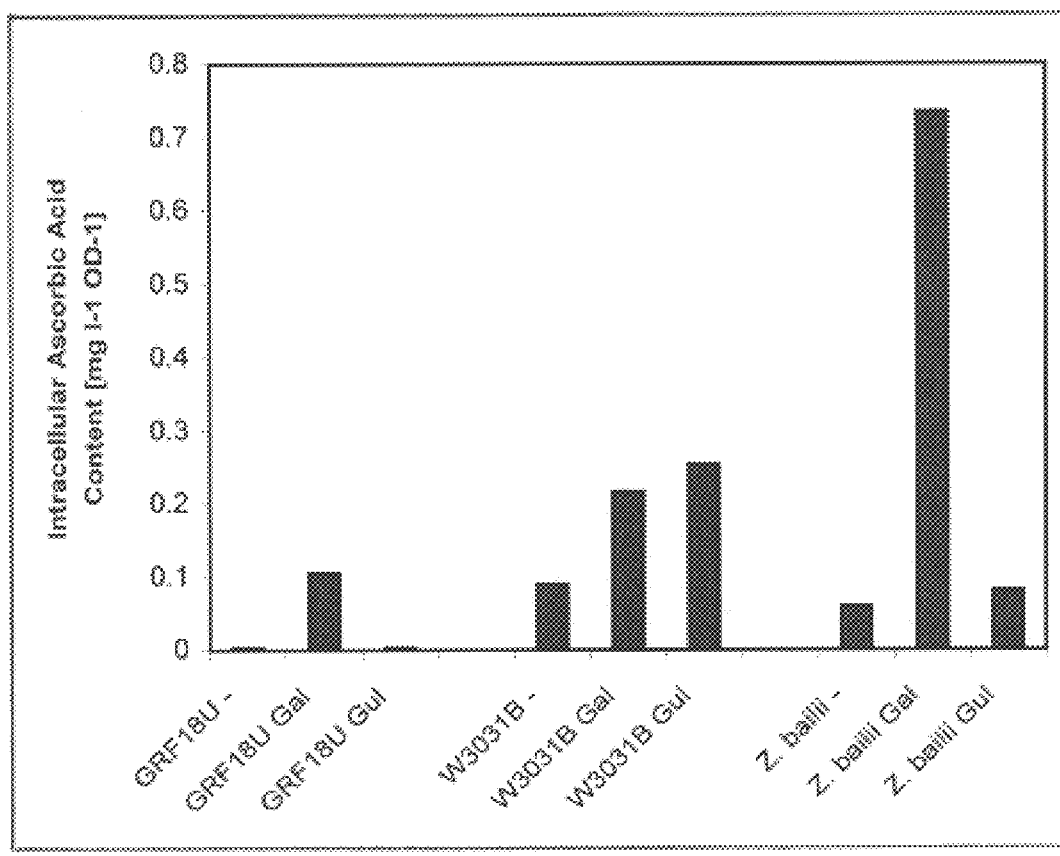
FIG. 3 shows the endogenous ability of yeasts to convert the precursors L-galactono-1,4-lactone (Gal) or L-gulono- 1,4-lactone (Gul) to ascorbic acid. Non-transformed yeast cells (S. cerevisiae GRF18U, W3031B and Z. bailii) were grown on mineral medium (2% glucose, 0.67% YNB) in the presence of 100 mM L-galactono-1,4-lactone or L-gulono-1,4-lactone, respectively, for 72 hr. (Initial $OD^{660}$ was 0.05); "–" signifies that no precursor was added. While ascorbic acid was accumulated within the cell, no ascorbic acid could be detected in the culture broth.

According to the literature, wild-type (wt) yeast comprises a D-arabinono-1,4-lactone oxidase activity with a broad substrate specificity (Huh W. K. et al., 1994, Eur. J. Biochem. 225, 1073–1079). Such activity has been demonstrated in vitro. To determine whether the substrates or the product could cross the cell membrane, we incubated three different yeast strains (*S. cerevisiae* GRF18U and W3031 B, as well as *Z. bailii*) with L-galactono-1,4-lactone (the last precursor of the plant biosynthetic pathway leading to ascorbic acid) or L-gulono-1,4-lactone (the last precursor of the animal metabolic pathway). As shown in FIG. 3, both of the substances can be internalized into the yeast cell and can be converted to ascorbic acid. No ascorbic acid was accumulated in the culture broth (not shown) but significant amounts were measured in whole cell extracts.

Figure 4:
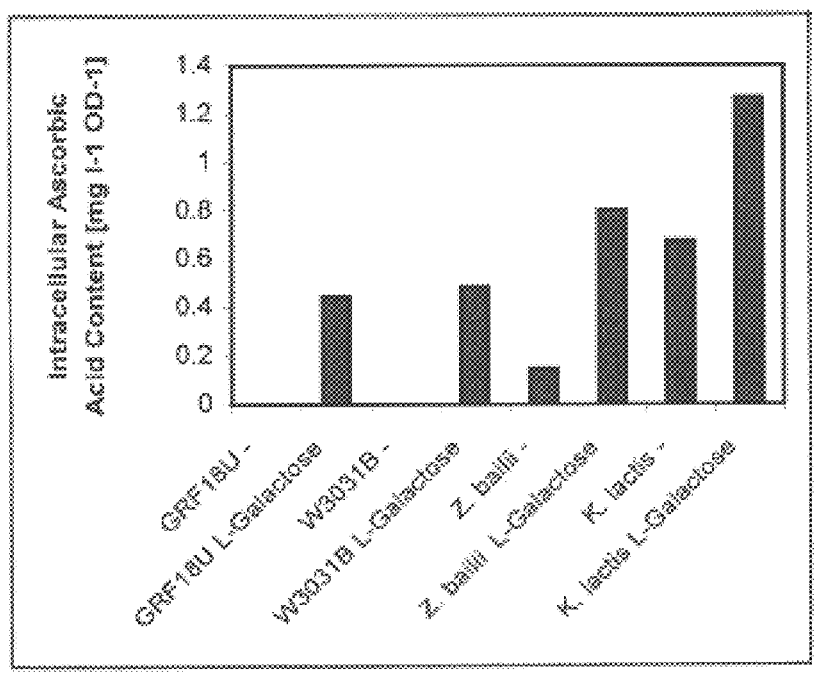
FIG. 4 shows the endogenous ability of yeasts to convert L-galactose to ascorbic acid. Non-transformed S. cerevisiae (GRF18U and W303 1 B), Z. bailii and K. lactis were grown on mineral medium (2% glucose, 0.67% YNB) starting from an $OD^{660}$ of 0.05 overnight. Then, 250 mg $1^{-1}$ L-galactose were added and the cultures were kept under standard conditions for another 24 hr before the determination of ascorbic acid. All of these strains accumulated ascorbic acid intracellulary while no ascorbic acid was measurable in the culture broth. (It is believed the high background in K. lactis is due to erythroascorbic acid, naturally present in this yeast species at higher concentrations than seen in S. cerevisiae).

The next prior precursor in the plant pathway is L-galactose. FIG. 4 shows the results of incubations of yeast cells with this substrate. *S. cerevisiae*, *Z. bailii*, and *K. lactis* are able to produce ascorbic acid from this compound, but also in this case ascorbic acid is accumulated to a significant amount inside of the cell (FIG. 4), but the concentration in the culture medium remains under the detection limit (not shown).

Figure 5:
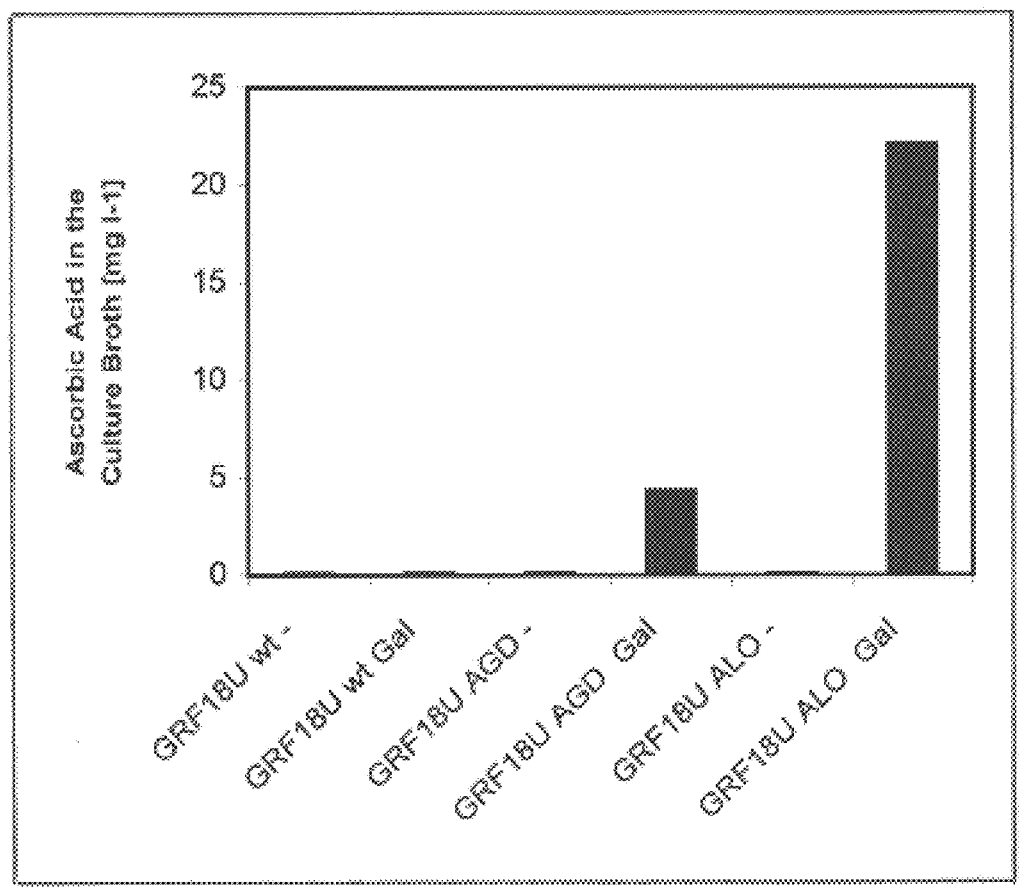
FIG. 5 shows the conversion of L-galactono-1,4-lactone to ascorbic acid by recombinant yeasts. S. cerevisiae GRF18U wt (control), or transformed with AGD or ALO, respectively, were grown on mineral medium (2% glucose, 0.67% YNB) starting from an $OD^{660}$ of 0.05 in the presence of 50 mM L-galactono-1,4-lactone (Gal) for 72 hr. While the control cells did not accumulate ascorbic acid in the culture medium, cells transformed with AGD or ALO unexpectedly accumulated considerable amounts (i.e. greater than background levels) of ascorbic acid in the culture medium. No ascorbic acid was detected in cultures without the addition of L-galactono-1,4-lactone (marked–).
Figure 6:
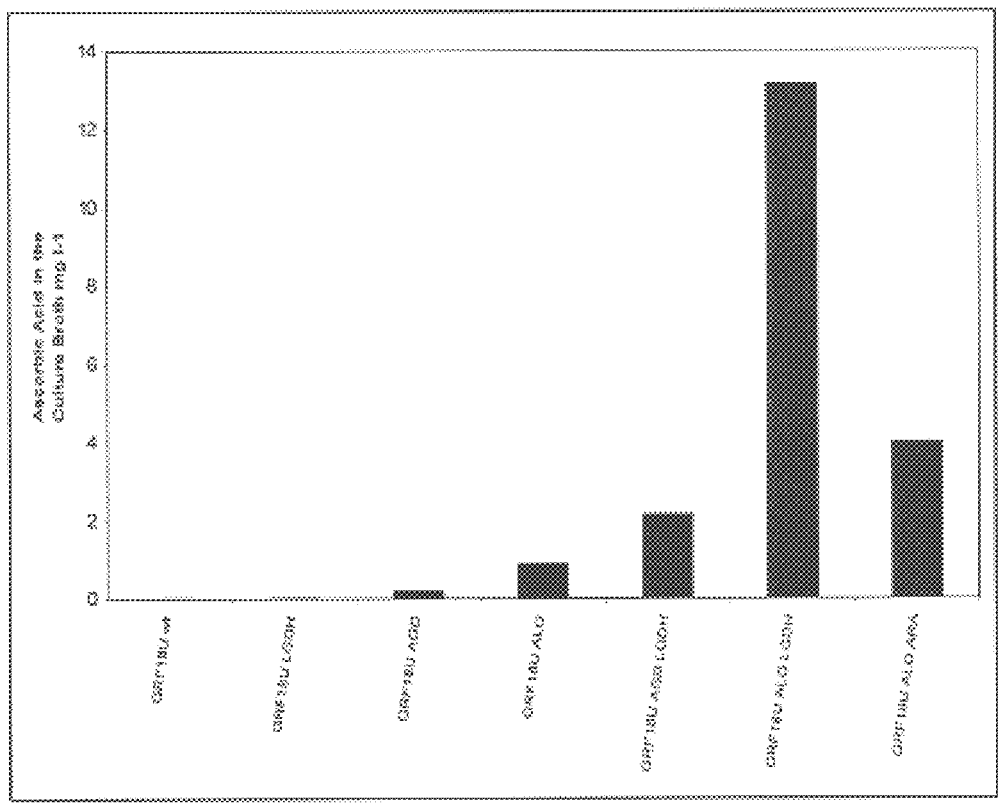
FIG. 6 shows the conversion of L-galactose to ascorbic acid by recombinant yeasts. S. cerevisiae GRF18U wt (control), transformed with LGDH; AGD; ALO; AGD and LGDH; ALO and LGDH; or ARA and ALO, respectively, were grown on mineral medium (2% glucose, 0.67% YNB) starting from an $OD^{660}$ of 0.05 over night. Then 250 mg $1^{-1}$ L-galactose were added and the cultures were kept under standard conditions for another 24 hr before the determination of ascorbic acid. The control cells or cells transformed with only LGDH did not accumulate ascorbic acid in the culture medium. Cells transformed with LGDH and either AGD or ALO, as well as cells transformed with ARA and ALO, accumulate considerable amounts (i.e. greater than background levels) of ascorbic acid in the medium.
Figure 7:
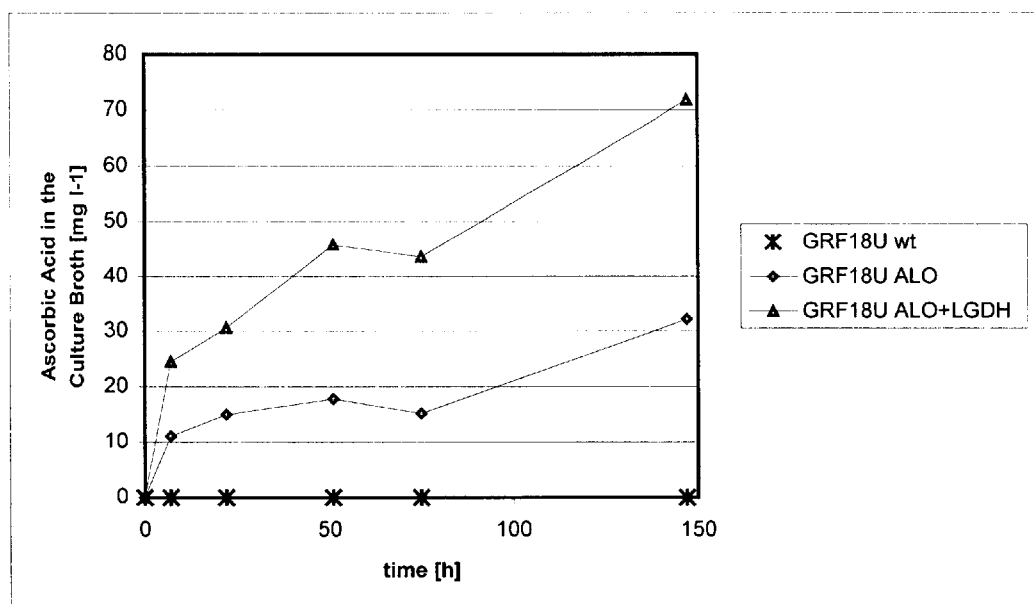
FIG. 7 shows the conversion of L-galactose to ascorbic acid in a high cell density culture of recombinant yeast. S. cerevisiae GRF18U wt (control) or transformed with ALO, or LGDH and ALO, respectively, were grown on mineral medium (2% glucose, 0.67% YNB) starting from an $OD^{660}$ of 0.05 over night. At time 0 the cells were concentrated 10 times and 250 mg $1^{-1}$ L-galactose were added and the cultures were kept under standard conditions for 6 days. At the times indicated samples were taken and the ascorbic acid concentration in the culture broth was measured. While the control cells did not accumulate ascorbic acid in the culture medium, cells transformed with ALO alone or ALO and LGDH accumulated considerable amounts (i.e. greater than background levels) of ascorbic acid in the medium.

3. Ascorbic Acid Production and Accumulation in the Medium From Transformed Yeasts We cloned the homologous genes of D-arabinono-1,4-lactone oxidase (ALO) and D-arabinose dehydrogenase (ARA), as well as the heterologous *A. thaliana* genes for L-galactono-1,4-lactone dehydrogenase (AGD) and L-galactose dehydrogenase (LGDH). These genes were cloned into available yeast expression vectors like outlined in materials and methods. In short, the plasmids are integrative and the TPI promoter, a naturally strong and constitutive promoter of *S. cerevisiae*, drives the expression of the genes in question. Upon incubation of *S. cerevisiae* GRF18U transformed with AGD or ALO with L-galactono-1,4-lactone, the cells not only accumulated ascorbic acid intracellularly (not shown), but also, surprisingly, accumulated considerable amounts of ascorbic acid into the culture broth (FIG. 5). This was also true for the same transformed cells incubated with L-galactose (FIG. 6). Cotransformation of L-galactose dehydrogenase or D-arabinose dehydrogenase significantly increased the ability of the respective yeast strain to convert L-galactose to ascorbic acid (FIG. 6). FIG. 7 shows data of a high-density culture converting L-galactose to ascorbic acid. The respective yeast strains were grown overnight in standard minimal medium. The next day, the cells were aseptically centrifuged and the pellet was resuspended in 1/10 of the supernatant to concentrate the cells 10 times. Then, 250 mg $l^{-1}$ of L-galactose were added and the cultures were incubated under standard conditions for 6 days. After 6 days the strain transformed with ALO and LGDH accumulated over 70 mg ascorbic acid per liter culture medium. 30 mg $l^{-1}$ ascorbic acid were accumulated intracellularly (not shown). Taking these two values together corresponds to a conversion of around 40% of the L-galactose added.

The following table summarizes the main examples reported in this invention.

|  |  |  | Production of Ascorbic acid | |
| --- | --- | --- | --- | --- |
| Examples of Yeast | Examples of Gene overexpressed | Examples of Converted precursors | intracellular | extracellular |
| S. cerevisiae | no | L-galactono-1,4-lactone<br>L-gulono-1,4-lactone<br>L-galactose | yes | no |
| K. lactis | no | L-galactose | yes | no |
| Z. bailii | no | L-galactono-1,4-lactone<br>L-gulono-1,4-lactone<br>L-galactose | yes | no |
| S. cerevisiae | AGD (from A. thaliana) | L-galactono-1,4-lactone | yes | no |
| S. cerevisiae | ARA | L-galactono-1,4-lactone | yes | yes |
| S. cerevisiae | LGDH (from A. thaliana) | L-galactose | yes | no |
| S. cerevisiae | LGDH (from A. thaliana) + ALO or AGD (from A. thaliana) | L-galactose | yes | yes |
| S. cerevisiae | ARA + ALO | L-galactose | yes | yes |
| S. cerevisiae | RGLO (from R. norvegicus) | L-gulono-1,4-lactone | Not det. | Not det. |

While the compositions and methods and yeast strains of this invention have been described in terms of preferred embodiments, it will be apparent to those of skill in the art that variations may be applied without departing from the concept, spirit and scope of the invention.

REFERENCES

The following references, to the extent that they provide exemplary procedural or other details supplementary to those set forth herein, are specifically incorporated herein by reference.

[1] Padh H. 1990, Cellular functions of ascorbic acid, Biochem. Cell Biol. 68, 1166–1173.

[2] U.S. Pat. No. 2,265,121

[3] Huh, W. K., Lee, B. H., Kim, S. T., Kim, Y. R., Rhie, G. E., Baek, Y. W., Hwang, C. S., Lee, S. J., Kang, S. O., 1998, D-Erythroascorbic acid is an important antioxidant molecule in S. cerevisiae, Mol. Microb. 30, 4, 895–903

[4] Wheeler, G. L., Jones, M. A., Smirnoff, N., 1998, The biosynthetic pathway of vitamin C in higher plants, Nature 393, 365–368

[5] Huh, W. K., Kim, S. T., Yang, K. S., Seok, Y. J., Hah, Y. C., Kang, S. O., 1994, Characterisation of D-arabinono-1,4-lactone oxidase from Candida albicans ATCC 10231, Eur. J. Biochem. 225, 1073–1079

[6] Kim, S. T., Huh, W. K., Kim, J. Y., Hwang, S. W., Kang, S. O., 1996, D-Arabinose dehydrogenase and biosynthesis of erythroascorbic acid in Candida albicans, BBA 1297, 1–8

[7] Kim, S. T., Huh, W. K., Lee, B. H., Kang, S. O., 1998, D-Arabinose dehydrogenase and its gene from Saccharomyces cerevisiae, BBA 1429, 29–39

[8] Roland, J. F., Cayle, T., Dinwoodie, R. C., Mehnert, D. W., 1986, Fermentation Production of Ascorbic Acid from L-Galactonic Substrate, U.S. Pat. No. 4,595,659

[9] Roland, J. F., Cayle, T., Dinwoodie, R. C., Mehnert, D. W., 1990, Bioconversion Production of Ascorbic Acid with L-Galactono-1,4-Oxidase, U.S. Pat. No. 4,916,068

[10] Lee, B. H., Huh, W. K., Kim, S. T., Lee, J. S., Kang, S. O., 1999, Bacterial Production of D-Erythroascorbic Acid and L-Ascorbic Acid through Functional Expression of Saccharomyces cerevisiae D-Arabinono-1,4-Lactone Oxidase in Escherichia coli, App.Env. Microb. 65, 10, 4685–4687

[11] Østergaard, J., Persiau, G., Davey, M. W., Bauw, G., Van Montagu, M., 1997, Isolation of a cDNA Coding for L-Galactono-γ-Lactone Dehydrogenase, an Enzyme involved in the Biosynthesis of Ascorbic Acid in Plants, J. Biol. Chem. 272, 48, 30009–30016

[12] Bauw, G. J. C., Davey, M. W., Østergaard, J., Van Montagu, M. C. E., 1998, Production of Ascorbic Acid in Plants, 1998, International Patent Application, WO98/50558

[13] Berry, A., Running, J., Severson, D. K., Burlingame, R. P., 1999, Vitamin C Production in Microorganisms and Plants, International Patent Application, WO99/64618

[14] Smirnoff, N., Wheeler, G., 1999, Plant Galactose Dehydrogenase, International Patent Application, WO099/33995

[15] Hancock, R. D., Galpin, J. R., and Viola, R. 2000, Biosynthesis of L-ascorbic acid (vitamin C) by Saccharomyces cerevisiae. FEMS Microbiol. Lett. 186, 245–250

[16] Nishikimi, M., Noguchi, E., Yagi, K., 1978, Occurrence in Yeast of L-Galactonolactone Oxidase Which is Similar to a Key Enzyme for Ascorbic Acid Biosynthesis in Animals, L-Gulonolactone Oxidase, Arch. Biochem. Biophys. 191, 2, 479–486

[17] Bleeg, H. S., Christensen, F., 1982, Biosynthesis of Ascorbate in Yeast, Purification of L-Galactono-1,4-lactone Oxidase with Properties Different from Mammalian L-Gulonolactone Oxidase, Eur. J. Biochem. 127, 391–96

[18] Sullivan, M. X., Clarke, H. C. N., 1955, A highly specific procedure for ascorbic acid, Assoc. Off. Agr. Chem. 38, 2, 514–518

[19] Lowry, O. H., Rosebrough, N. J., Farr, A. L., Randall, R. J., 1951, Protein Measurement with the Folin Phenol Reagent, J.Biol.Chem. 193, 265–275

[20] Minet, M., Dufour, M. E., Lacroute, F., 1992, Plant J., 2, 417–422
[21] Sambrook et al., Molecular Genetics: A Laboratory Manual, Cold Spring Harbor Laboratory Press.
[22] Gietz, R. D. and Schiestl, R. H., 1996, Transforming Yeast with DNA, Methods in Mol. and Cell. Biol.
[23] Kreger-van Rij, N. J. W., "The Yeasts," Vol. 1 of Biology of Yeasts, Ch. 2, A. H. Rose and J. S. Harrison, Eds. Academic Press, London, 1987.
[24] Brambilla, L., Bolzani, D., Compagno, C., Carrera, D., van Dijken, J. P., Pronk, J. T., Ranzi, B. M., Alberghina, L., Porro, D. 1999, NADH reoxidation does not control glycolytic flux during exposure of respiring Saccharomyces cerevisiae cultures to glucose excess, FEMS Microb. Lett. 171, 133–140
[25] Wésolowski-Louvel, M., Prior, C., Bornecque, D., Fukuhara, H. 1992, Rag-mutations involved in glucose metabolism in yeast: isolation and genetic characterization. Yeast 8, 711–719
[26] Kumar, M. 2000 Production of ascorbic acid using yeast, International patent application WO 00/34502

What is claimed is:

1. A method of generating ascorbic acid, comprising:
   a) obtaining a recombinant Saccharomyces yeast strain capable of converting an ascorbic acid precursor into ascorbic acid,
   b) culturing the recombinant yeast in a medium comprising the ascorbic acid precursor, wherein the recombinant yeast produces ascorbic acid with a yield greater than about 35% from the ascorbic acid precursor, and
   c) isolating the ascorbic acid.

2. The method of claim 1, wherein the yeast is selected from Saccharomyces cerevisiae (S. cerevisiae) strain GRF18U; or S. cerevisiae strain W3031B.

3. The method of claim 1, wherein the ascorbic acid precursor is selected from L-galactono-1,4-lactone; D-glucose; L-gulono-1,4-lactone; or L-galactose.

4. The method of claim 1, wherein the isolating step comprises lysing the yeast.

5. The method of claim 4, wherein the isolating step further comprises centrifugation, filtration, microfiltration, ultrafiltration, nanofiltration, liquid-liquid extraction, crystallization, enzymatic treatment with nuclease or protease, or chromatography.

6. The method of claim 1, wherein the recombinant yeast accumulates L-ascorbic acid in the medium at levels greater than background.

7. The method of claim 6, wherein the isolating step comprises chromatography, activated carbon, microfiltration, ultrafiltration, nanofiltration, liquid-liquid extraction, or crystallization.

8. The method of claim 1, wherein the yeast is functionally transformed with a coding region encoding L-galactose dehydrogenase (LGDH).

9. The method of claim 8, wherein the coding region encoding LGDH was isolated from Arabidopsis thaliana (A. thaliana).

10. The method of claim 8, wherein the functionally transformed yeast further comprises at least one coding region encoding an enzyme associated with the conversion of a carbon source to L-gulactose.

11. The method of claim 8, wherein the coding region is linked to a promoter active in the yeast.

12. The method of claim 11, wherein the promoter is the S. cerevisiae triosephosphateisomerase (TPI) promoter.

13. The method of claim 8, wherein the yeast is further functionally transformed with a coding region encoding D-arabinono-1,4-lactone oxidase (ALO).

14. The method of claim 13, wherein the coding region encoding the ALO is linked to a promoter active in the yeast.

15. The method of claim 14, wherein the promoter is the S. cerevisiae triosephosphateisomerase (TPI) promoter.

* * * * *

UNITED STATES PATENT AND TRADEMARK OFFICE
CERTIFICATE OF CORRECTION

PATENT NO.  : 6,630,330 B1  Page 1 of 1
DATED       : October 7, 2003
INVENTOR(S) : Danilo Porro and Michael Sauer It is certified that error appears in the above-identified patent and that said Letters Patent is hereby corrected as shown below:

Column 56,
Line 43, delete "L-gulactose" and insert -- L-galactose --.

Signed and Sealed this

Eighteenth Day of November, 2003

JAMES E. ROGAN
*Director of the United States Patent and Trademark Office*